(12) United States Patent
Howarth et al.

(10) Patent No.: US 6,638,959 B2
(45) Date of Patent: *Oct. 28, 2003

(54) MICROBIOLOGICAL CONTROL IN AQUEOUS SYSTEMS

(75) Inventors: Jonathan N. Howarth, Baton Rouge, LA (US); Christopher J. Nalepa, Baton Rouge, LA (US); Michael J. Sanders, Baton Rouge, LA (US); David L. Shelton, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/974,626

(22) Filed: Oct. 9, 2001

(65) Prior Publication Data

US 2002/0120000 A1 Aug. 29, 2002

Related U.S. Application Data

(63) Continuation-in-part of application No. 09/484,938, filed on Jan. 18, 2000, and a continuation-in-part of application No. 09/775,516, filed on Feb. 2, 2001.

(51) Int. Cl.⁷ .............................................. A01N 43/50
(52) U.S. Cl. .................. 514/389; 424/405; 424/406; 424/407; 424/408; 424/409; 424/417; 424/420; 424/421; 252/175; 252/388; 252/390
(58) Field of Search ................. 424/405–409, 424/417–420, 421; 574/389, 390; 252/175, 179, 180, 387, 388, 390, 394–396

(56) References Cited

U.S. PATENT DOCUMENTS 2,130,805 A  9/1938  Levine ........................ 210/28
2,392,505 A  1/1946  Rogers ...................... 260/309.5

(List continued on next page.)

FOREIGN PATENT DOCUMENTS

| CA | 1230825 | 12/1987 |
| CA | 2042430 | 11/1991 |

(List continued on next page.)

OTHER PUBLICATIONS

Gottardi Zentralli. Bacteriol., Paraoitenlrd, Abstract:Infektwnokr.MYG. ABT.1, 162(3–4)384–8, 1976.*
Corral et al., "Substitution in the Hydantoin Ring. III. Halogenation", J. Org. Chem., 1963, vol. 28, ppg. 1100–1104.
Jolles, "General Methods of Bromination", Bromine and its Compounds, 1966, Ernest Benn, London, ppg. 365.
Markish et al., "New Aspects on the Preparation of 1,3–Dibromo–5,5–Dimethylhydantoin", Ind. Eng. Chem. Res. 1995, vol. 34, ppg. 2125–2127.

(List continued on next page.)

*Primary Examiner*—Neil S. Levy
(74) *Attorney, Agent, or Firm*—Edgar E. Spielman, Jr.

(57) ABSTRACT

Microbiological control is achieved by continuously and inexpensively dosing water in contact with biofilm, or that comes into contact with biofilm, using a highly effective biocide that provides very effective microbiocidal control of planktonic microorganisms and of biofilm species, even where the biofilm infestations have been in existence for long periods of time and thus have encased themselves in a substantial quantity of slimy defensive polysaccharide layers or films. In addition, the biocide used makes possible significant reduction in copper and/or iron surfaces in contact with the water as compared to N,N'-bromochloro-5,5-dimethyl hydantoin. Still other advantages are made possible by the described technology.

24 Claims, 2 Drawing Sheets

BCDMH Vs DBDMH
Relative Distribution of Free & Total Cl
Simulated Cooling Water: pH 9.1, Temp 100 F, CH = 400 ppm, TA = 300 ppm

U.S. PATENT DOCUMENTS

| | | | |
|---|---|---|---|
| 2,398,598 A | 4/1946 | Rogers | 260/309.5 |
| 2,779,764 A | 1/1957 | Paterson | 260/309.5 |
| 2,795,556 A | 6/1957 | Quinn | 252/187 |
| 2,868,787 A | 1/1959 | Paterson | 260/248 |
| 2,920,997 A | 1/1960 | Wolf et al. | 167/33 |
| 2,971,959 A | 2/1961 | Waugh et al. | 260/309.5 |
| 2,971,960 A | 2/1961 | Waugh et al. | 260/309.5 |
| 3,121,715 A | 2/1964 | Waugh et al. | 260/248 |
| 3,147,259 A | 9/1964 | Paterson | 260/248 |
| 3,345,371 A | 10/1967 | Paterson | 260/192 |
| 3,626,972 A | 12/1971 | Lorenzen | 137/268 |
| 4,078,099 A | 3/1978 | Mazzola | 427/213 |
| 4,126,717 A | 11/1978 | Mazzola | 427/220 |
| 4,136,052 A | 1/1979 | Mazzola | 252/94 |
| 4,199,001 A | 4/1980 | Kratz | 137/268 |
| 4,242,216 A | 12/1980 | Daugherty et al. | 252/103 |
| 4,270,565 A | 6/1981 | King, Sr. | 137/268 |
| 4,293,425 A | 10/1981 | Price | 210/751 |
| 4,327,151 A | 4/1982 | Mazzola | 428/407 |
| 4,331,174 A | 5/1982 | King, Sr. | 137/268 |
| 4,427,692 A | 1/1984 | Girard | 424/273 R |
| 4,465,839 A | 8/1984 | Schulte et al. | 548/310 |
| 4,532,330 A | 7/1985 | Cole | 548/311 |
| 4,537,697 A | 8/1985 | Girard | 252/90 |
| 4,560,766 A | 12/1985 | Girard et al. | 548/311 |
| 4,571,333 A | 2/1986 | Hsiao et al. | 424/22 |
| 4,597,941 A | 7/1986 | Bottom et al. | 422/37 |
| 4,621,096 A | 11/1986 | Cole | 514/389 |
| 4,654,424 A | 3/1987 | Girard et al. | 548/311 |
| 4,659,359 A | 4/1987 | Lorenz et al. | 71/67 |
| 4,662,387 A | 5/1987 | King, Sr. | 137/268 |
| 4,677,130 A | 6/1987 | Puzig | 514/389 |
| 4,698,165 A | 10/1987 | Theyson | 210/755 |
| 4,713,079 A | 12/1987 | Chun et al. | 8/101 |
| 4,728,453 A | 3/1988 | Choy | 252/91 |
| 4,745,189 A | 5/1988 | Lee et al. | 544/221 |
| 4,780,197 A | 10/1988 | Schuman | 210/136 |
| 4,803,079 A | 2/1989 | Hsiao et al. | 424/468 |
| 4,867,895 A | 9/1989 | Choy | 252/91 |
| 4,919,841 A | 4/1990 | Kamel et al. | 252/186.26 |
| 4,925,866 A | 5/1990 | Smith | 514/389 |
| 5,076,315 A | 12/1991 | King | 137/268 |
| 5,137,563 A | 8/1992 | Valkanas | 71/64.07 |
| 5,218,983 A | 6/1993 | King | 137/1 |
| 5,338,461 A | 8/1994 | Jones | 210/755 |
| 5,339,889 A | 8/1994 | Bigham | 165/1 |
| 5,384,102 A | 1/1995 | Ferguson et al. | 422/264 |
| 5,403,813 A | 4/1995 | Lichti et al. | 504/116 |
| 5,422,126 A | 6/1995 | Howarth et al. | 424/723 |
| 5,476,116 A | 12/1995 | Price et al. | 137/268 |
| 5,565,109 A | 10/1996 | Sweeney | 210/755 |
| 5,565,576 A | 10/1996 | Hall et al. | 548/317.1 |
| 5,578,559 A | 11/1996 | Dolan et al. | 510/192 |
| 5,591,692 A | 1/1997 | Jones et al. | 504/124 |
| 5,603,941 A | 2/1997 | Farina et al. | 424/405 |
| 5,610,126 A | 3/1997 | Barford et al. | 510/191 |
| 5,614,528 A | 3/1997 | Jones et al. | 514/258 |
| 5,670,451 A | 9/1997 | Jones et al. | 504/134 |
| 5,750,061 A | 5/1998 | Farina et al. | 264/117 |
| 5,753,602 A | 5/1998 | Hung et al. | 510/192 |
| 5,756,440 A | 5/1998 | Watanabe et al. | 510/191 |
| 5,763,376 A | 6/1998 | Ward et al. | 510/191 |
| 5,780,641 A | 7/1998 | Yerushalmi et al. | 548/320.5 |
| 5,859,060 A | 1/1999 | Platt | 514/569 |
| 5,942,153 A | 8/1999 | Heydel | 252/187.33 |
| 5,958,853 A | 9/1999 | Watanabe | 510/192 |
| 5,972,864 A | 10/1999 | Counts | 510/192 |
| 5,981,461 A | 11/1999 | Counts et al. | 510/365 |
| 5,984,994 A | 11/1999 | Hudson | 71/28 |

FOREIGN PATENT DOCUMENTS

| | | |
|---|---|---|
| CA | 2163596 | 9/1996 |
| EP | 0177645 | 4/1986 |
| EP | 0206725 | 12/1986 |
| EP | 0228593 | 7/1987 |
| EP | 0581826 | 9/1995 |
| GB | 1054243 | 1/1967 |
| GB | 2273106 | 6/1994 |
| JP | 56158333 | 12/1981 |
| JP | 7299468 | 11/1995 |
| WO | 8910696 | 11/1989 |
| WO | 9630491 | 10/1996 |
| WO | 9715652 | 5/1997 |
| WO | 9720546 | 6/1997 |
| WO | 9720909 | 6/1997 |
| WO | 9743264 | 11/1997 |
| WO | 9743392 | 11/1997 |
| WO | 0034186 | 6/2000 |
| WO | 0153209 | 7/2001 |

OTHER PUBLICATIONS

Orazi et al., "Halogenacion con 3–Bromo–5,5–Dimetil–Hidantoina", Anales Assoc. Quim. Argentina, 1949, vol. 37, ppg. 192–196. (Not translated).

Orazi et al., "Halogenacion Con 1–3–Dibromo–5, 5–Dimetil–Hidantoina", Anales Assoc. Quim. Argentina, 1950, vol. 38, ppg. 5–11. (Not translated).

March, "Advanced Organic Chem.", 1992, $4^{th}$ Edition, ppg. 639–640.

HCAPLUS Abstract of JP 07171576 A2 issued 1995.

HCAPLUS Abstract of JP 07277912 A2 issued 1995.

HCAPLUS Abstract of JP 08027119 A2 issued 1996.

Chowhan et al., "Hardness Increase Induced by Partial Moisture Loss in Compressed Tablets and Its Effect on In Vitro Dissolution", J. Pharm. Sciences, Oct. 1978, vol. 67, No. 10, ppg. 1385–1389.

Krycer et al., "An Evaluation of Tablet Binding Agents II. Pressure Binders", Powder Technology, 1983, vol. 34, ppg. 53–56.

Petterson, "N–Halogen Compounds. I. Decomposition of 1,3–Dichloro–5,5–dimethylhydantoin in Water at pH 9", J. Org. Chem., 1959, vol. 24, ppg. 1414–1419.

HCAPLUS Abstract of JP 08239699 A2 issued 1996.

HCAPLUS Abstract of JP 09087684 A2 issued 1997.

HCAPLUS Abstract of JP 09227317 A2 issued 1997.

Author unknown, "Big Brother Brominator—Brominators", Bulky Systems Website, < http://www.bulkysystemsinc.com/brominator.html> (Visited Aug. 10, 2001). 1 page.

Author unknown, "Bio Lab Brominator", Conely Company Website, < http://www.conelyco.com/Pool–Spa/parts/bio-brom.htm> (Visited Aug. 10, 2001) 2 pages.

Hayward Pool Products Owner's Guide, Installation and Operating Instructions, "Hayward Chemical Feeder", Models C250CF, C500CF, C1100CF, C1800CF, C2400CF,—1998—4 pages.

Pentair Pool Products Brochure, "Rainbow Model 320 Automatic Chlorine/Bromine In–line Feeder", "Saves Time, Reduces Manual Handling of Chemicals", date unknown, 7 pages. '99.

Sani–King Perform–Max Pool Sanitizer Instruction Guide, Models 910, 940, & 980 (Inline) and Models 930 & 960 (Off–line), date unknown, 16 pages. Prior to Jan. 18, 2000.

Sani–King Spa Feeder Product Brochure Model 740 from King Technology Website, < http://www.kingtechnology.com/spafeeder.htm> Visited (Aug. 10, 2001), 2000, 4 pages.

Sani–King Adjust–A–Flo Product Brochure from King Technology Website < http://www.kingtechnology.com/spafeeder.htm> (Visited Aug. 10, 2001), 2000, 1 page.

Sani–King Perform–Max Sanitizers for Inground Pools Product Brochure for Model 940 & 960 from King Technology Website, <http://www.kingtechnology.com/perfermaxIG.htm> , visited Aug. 10, 2001, 2000, 1 page.

Sani–King Perform–Max Sanitizers for Above Ground Pools Product Brochure Model 910 & 930 from King Technology Website, <http://www.kingtechnology.com/perfermaxIG.htm>, visited Aug. 10, 2001, 2000, 1 page.

Discount Pool & Spa Supplies, Automatic Chlorinators and Chemical Feeders Website, < http://www.discountpoolsupplies.com/Chemfeeders/> Visited Aug. 10, 2001, 3 pages.

Al–Zahrani, S.M.; "*Utilization of Polyethylene and Paraffin Waxes as Controlled Delivery Systems for Different Fertilizers*"; *Ind. Eng. Chem. Res., 2000*; vol. 39; pp. 369–371.

* cited by examiner

MICROBIOLOGICAL CONTROL IN AQUEOUS SYSTEMS

REFERENCE TO RELATED APPLICATIONS

This is a continuation-in-part of commonly-owned copending application Ser. No. 09/484,938, filed Jan. 18, 2000, and commonly-owned copending application Ser. No. 09/775,516, filed Feb. 2, 2001.

REFERENCE TO OTHER COMMONLY-OWNED APPLICATIONS

Commonly-owned copending application Ser. No. 09/323,348, filed Jun. 1, 1999; Ser. Nos. 09/483,896; 09/484,687; 09/484,844; 09/484,891; 09/487,816 each filed Jan. 18, 2000; Ser. No. 09/778,228, filed Feb. 6, 2001; and Ser. No. 09/893,581, filed Jun. 28, 2001 relate to subject matter that may be of interest in connection with the present subject matter.

BACKGROUND

Persons using biocidal agents in the biocidal treatment of water customarily, if not universally, refer to "free chlorine" level as a measure of biocidal control. To achieve "free chlorine" levels in water treatment, solid materials are often preferred because of their high weight percent activity. N,N'-bromochloro-5,5-dimethylhydantoin (BCDMH) has been one of the most widely-used solid sources of "free chlorine" for water treatment. One of the features emphasized for BCDMH by suppliers of BCDMH is that in use, the combined chlorine from the biocide regenerates "free chlorine" by reaction with inactive bromide species formed during the water treatment operation. In other words, the chlorine atom in the initial N,N'-bromochloro-5,5-dialkylhydantoin is said to be a precursor for additional "free chlorine" for sanitation purposes.

While effective, BCDMH does have certain heretofore-unrecognized drawbacks. For example, when used at conventional dosage levels in treating industrial water systems, the rate of corrosion of iron and copper surfaces in contact with the treated water is higher than desired. In addition, the rate of consumption of the BCDMH in treating the water for effective biocidal action is significantly higher than is desirable from the standpoint of the consumer. Further, during usage the amount of halogen residual in the treated water is lower than would be desired.

Further shortcomings of BCDMH are that in use, BCDMH hydrolyzes into HOBr and HOCl both of which register as "free chlorine" species in commonly-used standard test procedures. These methods for determining "free chlorine" levels in treated water, involve use of a reagent known as DPD (i.e., N,N'-diethyldiphenylenediamine) and a buffer, and the results of such analyses are commonly used, if not universally used, as the basis for determining the quantity of a halogen-containing microbiocidal agent to be used for water treatment. Heretofore, consumers of BCDMH have only been concerned with the level of "free chlorine" provided by a given quantity of that biocidal material. What has not been realized by such consumers is the amount of "total chlorine" being utilized in order to achieve the requisite "free chlorine" level. As a consequence, the consumer has not had available a yardstick by which to determine the true economic efficiency of using BCDMH as a biocidal agent in the treatment of water. To achieve optimum economic efficiency, the consumer should have available for use a biocidal agent in which the amount of "free chlorine" released into the water corresponds closely to the "total chlorine" content of the biocidal agent.

In the event a biocidal agent provides a relatively small amount of "free chlorine" in relation to its "total chlorine" content, it has been deemed necessary to utilize a relatively large amount of such agent in order to achieve microbiological control. This in turn means high levels of halogenated materials are released into the environment. If on the other hand, a biocidal agent could provide to the water an amount of "free chlorine" that closely corresponds to the "total chlorine" content of the biocidal agent, effective microbiological control could be realized by use of much smaller dosages and with consequent minimal adverse impact upon the environment.

Also, while reasonably effective as a microbiocide, BCDMH is not as effective against biofilms tested to date as would be desired. Biofilms are bacterial films which tenaciously adhere to surfaces in contact with water such as heat exchanger surfaces, conduit interiors, filters, and other processing equipment. These films are very undesirable because they can harbor dangerous pathogens, and cause damage to the surfaces to which they have become attached. Moreover, the bacteria form a slime layer of extra-cellular polysaccharide which affords protection to the bacteria and in addition constitute an effective barrier against penetration of biocidal agents used in an attempt to combat such bacteria. In situations where the water is prone to development of calcium carbonate scale, the presence of such gelatinous extra-cellular polysaccharides can result in the formation of layers of scale bonded to the substrate surface by the gelatinous polysaccharides. Polysaccharide films and films of scale bonded by means of polysaccharides can greatly interfere with the operation of heat exchangers by virtue of their insulating characteristics, and can markedly interfere with the functioning of filters and the flow of water through pipes and conduits by virtue of the clogging tendencies of such polysaccharide films.

It would therefore be of considerable advantage if these drawbacks could be avoided in actual practice.

BRIEF SUMMARY OF THE INVENTION

This invention involves, inter alia, the discovery not only of the existence of a number of these drawbacks, but that it is indeed possible to avoid each and every one of these drawbacks in a highly efficient manner. Moreover, this invention makes it possible to continuously and inexpensively dose water in contact with biofilm, or that comes into contact with biofilm, using a highly effective biocide that provides very effective microbiocidal control of planktonic microorganisms and of biofilm species, even where the biofilm infestations have been in existence for long periods of time and thus have encased themselves in a substantial quantity of slimy defensive polysaccharide layers or films.

Accordingly, in one of its embodiments this invention provides a method of achieving highly effective "free chlorine" levels in treating with a biocide water that is or that comes into contact with at least one iron or copper surface, which method comprises introducing into said water, preferably but not necessarily continuously or substantially continuously, an effective biocidally active amount of at least one 1,3-dibromo-5,5-dialkylhydantoin that provides in the water a highly effective "free chlorine" level that is within 90% of the "total chlorine" level of the water, and that reduces the rate of corrosion of said iron or copper with which the water is or comes into contact as compared to N,N'-bromochloro-5,5-dimethylhydantoin.

In another of its embodiments this invention provides a method of achieving highly effective "free chlorine" levels in treating water with a biocide, which method comprises introducing into said water, preferably but not necessarily continuously or substantially continuously, an effective biocidally active amount of at least one 1,3-dibromo-5,5-dialkylhydantoin that provides in the water a highly effective "free chlorine" level that is within 90% of the "total chlorine" level in the water, and that enables the rate of biocide consumption to be reduced as compared to N,N'-bromochloro-5,5-dimethylhydantoin. In this embodiment it is further preferred that the water being treated is or comes into contact at least one surface of iron or copper so that the rate of corrosion of said iron or copper is reduced as compared to N,N'-bromochloro-5,5-dimethylhydantoin.

In each of the above embodiments it is particularly preferred to effect the introduction of the 1,3-dibromo-5,5-dialkylhydantoin(s) into the water continuously or substantially continuously by use of a dispenser, especially a floating dispenser, containing the 1,3-dibromo-5,5-dialkylhydantoin(s), more preferably in granular form.

The granules of 1,3-dibromo-5,5-dialkylhydantoin(s) used in the dispenser can be granules formed with or without use of one or more added substances contributing binding strength to the granules.

Still more preferably the granules of 1,3-dibromo-5,5-dialkylhydantoin(s) used in the dispenser are granules of this invention having one or both of the following characteristics and even more preferably both of the following characteristics:

a) an average crush strength of at least about 15 pounds per inch of thickness; and b) an average size in the range of about 40 U.S. standard mesh size to about ⅜-inch.

In another preferred embodiment the granules of this invention used in the dispenser are formed using a non-hydrophobic added substance contributing binding strength to the granules. The term "non-hydrophobic" is used herein to denote that the added substance in the amount present in the granules should not prevent, because of its resistance toward water, the granules from releasing to the water enough biocidal species (e.g., "free bromine") to provide an acceptable amount of biocidal activity in the water being treated. Thus while the added substance in its pure state may be hydrophobic, if used in a small enough amount as not to prevent the granules from releasing to the water enough biocidal species (e.g., "free bromine") to provide an acceptable amount of biocidal activity in the water being treated, the substance is deemed "non-hydrophobic" when used in such an amount.

In yet another preferred embodiment the granules of this invention used in the dispenser are formed using a suitable binder quantity of a micronized synthetic polyolefin-based hydrocarbon wax and/or a micronized synthetic polyfluorocarbon wax. These waxes so used are compatible with the active ingredient. In still another preferred embodiment the granules of this invention used in the dispenser are free of any added substance contributing binding strength or hardness to the granules.

The 1,3-dibromo-5,5-dialkylhydantoin(s) used in the practice of the various embodiments of this invention are typically those in which one of the alkyl groups in the 5-position is a methyl group and in which the other alkyl group in the 5-position has in the range of 1 to 4 carbon atoms. Most preferred for this use is 1,3-dibromo-5,5-dialkylhydantoin.

Other embodiments include a biocidal composition which comprises granules of at least one 1,3-dibromo-5,5-dialkylhydantoin having a crush strength of at least 15 pounds per inch of granule thickness, and preferably at least 20 pounds per inch of granule thickness, and an average size in the range of about 40 U.S. standard mesh size to about ⅜-inch, such 1,3-dibromo-5,5-dialkylhydantoin(s) being characterized in that one of the alkyl groups in the 5-position is a methyl group and the other alkyl group in the 5-position has in the range of 1 to 4 carbon atoms, the granules being devoid of any additive therein conferring binding or hardening action to the granules. A particularly preferred composition of this type is one in which the at least one 1,3-dibromo-5,5-dialkylhydantoin is 1,3-dibromo-5,5-dimethylhydantoin and in which the granules are able to be dissolved in quiescent water that is at a temperature of 25° C. at a rate such that 60 minutes after immersing the granules in quiescent water, the water contains in the range of about 75 to about 430 mg/L of "free chlorine" per gram of granules that were immersed in the water.

Other embodiments, features, and advantages of this invention will be still further apparent from the ensuing description and appended claims.

FURTHER DETAILED DESCRIPTION

Figure 1:
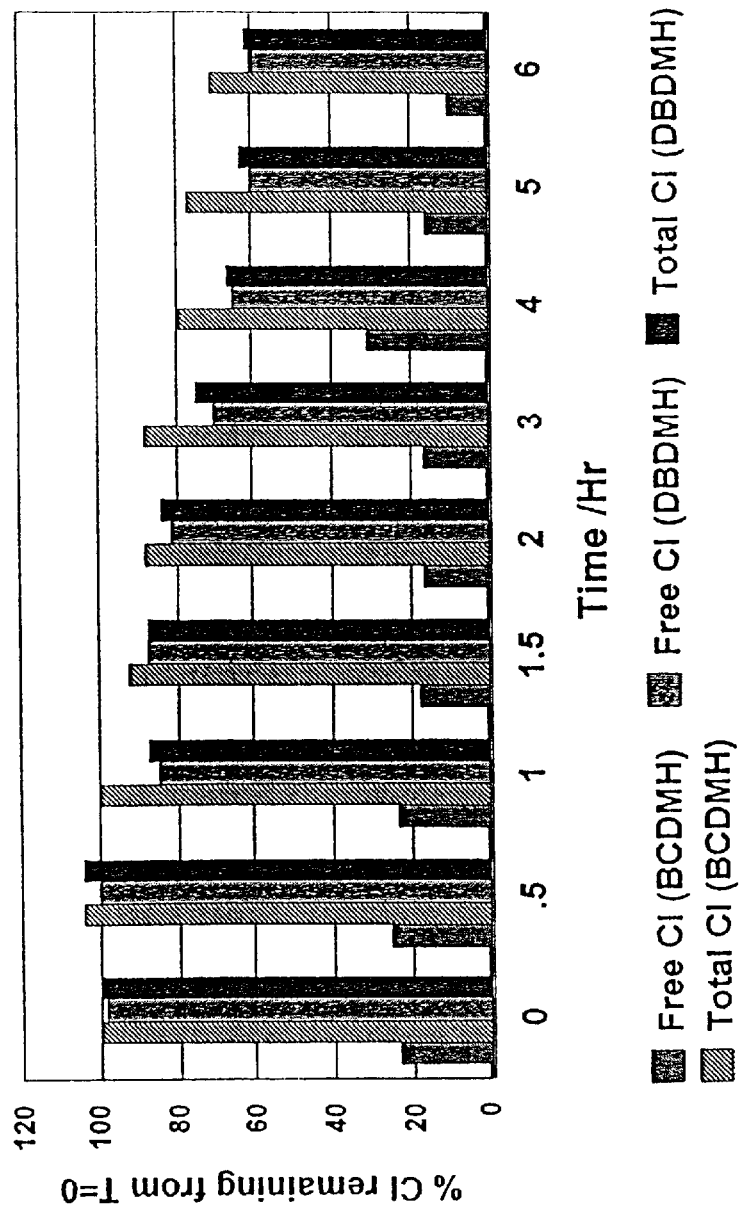
FIG. 1 is a graphical representation of the results of standard "free chlorine" and "total chlorine" tests performed on simulated cooling water solutions dosed with BCDMH or DBDMH, all as described in detail in Example 1 hereinafter.

At the outset it should be understood that the terms "free chlorine" and "total chlorine" are terms commonly used by persons in the fields of industrial and recreational water treatment. The values for the levels of "free chlorine" and "total chlorine" in the water are determined by use of appropriate standard test procedures which differentiate between the two. Further, the terms "free chlorine" and "total chlorine" are not restricted to just chlorine species in the water but rather, include certain bromine species in the water as well. Thus in a case where a biocidal agent used in treating the water contains both bromine and chlorine atoms (e.g., BCDMH), the "free chlorine" and "total chlorine" levels determined in the respective appropriate test procedures used would include quantification of the sum of the bromine species and chlorine species present that respond to the respective tests. The sum of these respective levels is reported, however, as "free chlorine" or "total chlorine", depending on the test used. Similarly, if the water treating agent used contains bromine atoms but no chlorine atoms, the "free chlorine" and "total chlorine" levels determined in the respective appropriate standard test procedures used would involve quantification of the level of bromine species present that respond to the respective tests. Thus although the halogen species actually present in such case are bromine-containing species, the levels present as determined in the respective tests would be reported as "free chlorine" and "total chlorine", respectively.

One of the many features of this invention is that 1,3-dibromo-5,5-dimethylhydantoin and probably other 1,3-dibromo-5,5-dialkylhydantoins used in the practice of this invention are able, at least in industrial water systems at pH of at least about 8, to provide to the water an amount of "free chlorine" that closely corresponds to the "total chlorine"

content of the biocidal agent thereby enabling both better economic efficiency for the consumer and effective microbiological control with small dosages and minimal adverse impact upon the environment. Generally, the "total chlorine" level in water of pH of at least 8 freshly treated with 1,3-dibromo-5,5-dimethylhydantoin is no more than about 10% higher than the "free chlorine level" of the water. Consequently the use of one or more 1,3-dibromo-5,5-dialkylhydantoins such as DBDMH as a water treating agent, especially when used in the treatment of industrial cooling water, is highly effective from an economic standpoint and highly desirable from an environmental standpoint. That is to say, the dosage levels of the 1,3-dibromo-5,5-dialkylhydantoins such as DBDMH needed to provide effective microbiological control with respect to such undesirable organisms and pathogens as bacteria, algae, and biofilms, are relatively low compared to dosage levels of BCDMH required for the same degree of control, especially in industrial cooling water. Moreover, the levels of halogenated materials released to the environment are much smaller when using a water-soluble dialkyldibromohydantoin such as DBDMH as compared to BCDMH.

Heretofore it has been widely believed that all bromine species dissolved in the water respond positively in the standard "free chlorine" test procedure. However, one of the features of this invention is the discovery that this universal belief is erroneous when the "free chlorine" test procedure is applied to recreational water, cooling water, process water, and wastewater, that contains bromine species, and especially to cooling water, process water, and wastewater that is has a pH above about 8.0. Under these conditions the dibromo-containing microbiocides used pursuant to this invention can give vastly superior values for "free chlorine" as compared to the corresponding bromochloro microbiocides as evidenced by the results described herein in which comparisons were made between DBDMH and BCDMH.

For example, it has been found that when water having a pH above about 8.0 is treated water with BCDMH to reach a desired "free chlorine" level, the amount of BCDMH being used is far greater than necessary to achieve a given level of microbiocidal effectiveness. This in turn means that the consumer has purchased and is using much more of the microbiocidal agent than necessary. As a consequence, there are involved both an economic penalty due to excessive consumption, and an environmental penalty due to release of excessive quantities of less biocidally-active halogen species to the environment.

Nevertheless, the "free chlorine" level in water treated with a halogen-releasing biocidal agent remains the yardstick by which microbiocidal performance is measured. Species which respond to the standard "free chlorine" test are HOCl and HOBr. Any other form of soluble halogen species do not respond to the standard "free chlorine" test. Such non-responsive species include, for example, chlorine species bound to a nitrogen atom. On the other hand, the standard "total chlorine" test measures both HOBr and HOCl, and any halogen species that do not respond to the standard "free chlorine" test.

The standard tests for determination of "free chlorine" and "total chlorine" are based on classical test procedures devised by Palin in 1974. See A. T. Palin, "Analytical Control of Water Disinfection With Special Reference to Differential DPD Methods For Chlorine, Chlorine Dioxide, Bromine, Iodine and Ozone", *J. Inst. Water Eng.*, 1974, 28, 139. While there are various modernized versions of the Palin procedures, the version of the tests for "free chlorine" and "total chlorine" used and to be used as the standard in connection with this invention, are fully described in *Hach Water Analysis Handbook,* 3rd edition, copyright 1997. The procedure for "free chlorine" is identified in that publication as Method 8021 appearing on page 335, whereas the procedure for "total chlorine" is Method 8167 appearing at page 379. Briefly, the "free chlorine" test involves introducing to the halogenated water a powder comprising DPD indicator powder and a buffer. "Free chlorine" present in the water reacts with the DPD indicator to produce a red to pink coloration. The intensity of the coloration depends upon the concentration of "free chlorine" species present in the sample. This intensity is measured by a colorimeter calibrated to transform the intensity reading into a "free chlorine" value in terms of mg/L $Cl_2$. Similarly, the "total chlorine" test also involves use of DPD indicator and buffer. In this case, KI is present with the DPD and buffer whereby the halogen species present, including nitrogen-combined halogen, reacts with KI to yield iodine species which turn the DPD indicator to red/pink. The intensity of this coloration depends upon the sum of the "free chlorine" species and all other halogen species present in the sample. Consequently, this coloration is transformed by the colorimeter into a "total chlorine" value expressed as mg/L $Cl_2$.

To convert "free chlorine" and "total chlorine" values into "free bromine" and "total bromine" values, the respective value for "free chlorine" or "total chlorine" is multiplied by 2.25.

An noted above, the 1,3-dibromo-5,5-dialkylhydantoins (DBDAH) biocidal water treating agents used in the practice of this invention provide a high level of both "free chlorine" and "total chlorine", and these levels are close together thus making them very desirable water treating agents. Not only are such agents highly effective as microbiocidal agents, but in addition are environmentally friendly and highly cost-effective, especially when used in the form of granules, and most especially when the granules are devoid of any binder or other substance increasing the hardness of the granules.

The 1,3-dibromo-5,5-dialkylhydantoins utilized in the practice of this invention are those in which one of the alkyl groups in the 5-position is a methyl group and the other alkyl group in the 5-position is an alkyl group having in the range of 1 to 4 carbon atoms. Thus the biocides used in this invention comprise 1,3-dibromo-5,5-dimethylhydantoin, 1,3-dibromo-5-ethyl-5-methylhydantoin, 1,3-dibromo-5-n-propyl-5-methylhydantoin, 1,3-dibromo-5-isopropyl-5-methylhydantoin, 1,3-dibromo-5-n-butyl-5-methylhydantoin, 1,3-dibromo-5-isobutyl-5-methylhydantoin, 1,3-dibromo-5-sec-butyl-5-methylhydantoin, 1,3-dibromo-5-tert-butyl-5-methylhydantoin, and mixtures of any two or more of them. Of these biocidal agents, 1,3-dibromo-5-isobutyl-5-methylhydantoin, 1,3-dibromo-5-n-propyl-5-methylhydantoin, and 1,3-dibromo-5-ethyl-5-methylhydantoin are, respectively, preferred, more preferred, and even more preferred members of this group from the cost effectiveness standpoint. Of the mixtures of the foregoing biocides that can be used pursuant to this invention, it is preferred to use 1,3-dibromo-5,5-dimethylhydantoin as one of the components, with amixture of 1,3-dibromo-5,5-dimethylhydantoin and 1,3-dibromo-5-ethyl-5-methylhydantoin being particularly preferred. The most preferred biocide employed in the practice of this invention is 1,3-dibromo-5,5-dimethylhydantoin.

When a mixture of two or more of the foregoing biocides is made up or used pursuant to this invention, the individual biocides of the mixture can be in any proportions relative to each other.

The dosage levels of the 1,3-dibromo-5,5-dialkylhydantoins in water systems treated pursuant to this invention can be varied within relatively wide limits, In general, the amount of DBDAH used is a biocidally effective amount, e.g., an amount which is at least sufficient to achieve substantial microbiological control, if not complete microbiological control, in the water being treated and/or substantial biofilm eradication, if not complete biofilm eradication, from the surfaces in contact with the water system being treated. Typically, dosages of 1,3-dibromo-5,5-dimethylhydantoin used for this purpose will fall within the range of about 0.1 to about 4.5 milligrams of "free chlorine" per liter of water (which corresponds to about 0.2 to about 10 milligrams of "free bromine" as $Br_2$, per liter of water). Preferably, such dosages are in the range of about 0.1 to about 2 milligrams of "free chlorine" per liter of water (which corresponds to about 0.2 to about 5 milligrams of "free bromine" as $Br_2$, per liter of water). However, departures from these ranges are permissible and are within the scope of this invention, provided that the departures result in sufficient microbiological control in accordance with the needs of the occasion, including applicable governmental regulations. These concentrations are determinable by use of the DPD test procedure.

It is to be understood that in the practice of this invention it is not necessary to perform the specified tests every time a body of water is to be dosed with DBDAH, or, in the case of certain embodiments, corresponding N,N-bromochloro-5,5-dialkylhydantoin(s) (BCDAH) for baseline values. Instead, as made clear by the use of the term "determinable" (i.e., able to be determined), the testing should be done when deemed necessary or desirable to either establish the requisite dosage of DBDAH or BCDAH, or to check or confirm that the proposed dosage complies with this invention and thus will make available the economic and environmental benefits resulting from the practice of this invention.

When it is desired to conduct the appropriate testing any suitable method of determining "free chlorine" and "total chlorine" can be used, but in the event of any conflicting data or dispute as between different parties, the full procedure set forth below entitled "DBDAH and BCDMH Test Procedure" is to be used to resolve the issue in connection with any embodiment of this invention.

DBDAH and BCDMH Test Procedure

1. To determine the amount of species present in the water which respond to the "free chlorine" and "total chlorine" tests, the water sample should be analyzed within a few minutes of being taken, and preferably immediately upon being taken.
2. Hach Method 8021 for testing the amount of species present in the water sample which respond to the "free chlorine" test involves use of the Hach Model DR 2010 colorimeter. The stored program number for chlorine determinations is recalled by keying in "80" on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. Using the 10 mL cell riser, this is admitted to the sample compartment of the Hach Model DR 2010, and the shield is closed to prevent stray light effects. Then the ZERO key is depressed. After a few seconds, the display registers 0.00 mg/L $Cl_2$. To second cell, the contents of a DPD Free Chlorine Powder Pillow are added. This is shaken for 10–20 seconds to mix, as the development of a pink-red color indicates the presence of species in the water which respond positively to the DPD test reagent. Within one minute of adding the DPD "free chlorine" reagent to the 10 mL of water in the sample cell, the blank cell used to zero the instrument is removed from the cell compartment of the Hach Model DR 2010 and replaced with the test sample to which the DPD "free chlorine" test reagent was added. The light shield is then closed as was done for the blank, and the READ key is depressed. The result, in mg/L $Cl_2$ is shown on the display within a few seconds. This is the "free chlorine" level of the water sample under investigation.
3. Hach Method 8167 for testing the amount of species present in the water sample which respond to the "total chlorine" test involves use of the Hach Model DR 2010 colorimeter. The stored program number for chlorine determinations is recalled by keying in "80" on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. To the second cell, the contents of a DPD Total Chlorine Powder Pillow are added. This is shaken for 10–20 seconds to mix, as the development of a pink-red color indicates the presence of species in the water which respond positively to the DPD "total chlorine" test reagent. On the keypad, the SHIFT TIMER keys are depressed to commence a three minute reaction time. After three minutes the instrument beeps to signal the reaction is complete. Using the 10 mL cell riser, the blank sample cell is admitted to the sample compartment of the Hach Model DR 2010, and the shield is closed to prevent stray light effects. Then the ZERO key is depressed. After a few seconds, the display registers 0.00 mg/L $Cl_2$. Then, the blank sample cell used to zero the instrument is removed from the cell compartment of the Hach Model DR 2010 and replaced with the test sample to which the DPD "total chlorine" test reagent was added. The light shield is then closed as was done for the blank, and the READ key is depressed. The result, in mg/L $Cl_2$ is shown on the display within a few seconds. This is the "total chlorine" level of the water sample under investigation.
4. Where it is desired to convert mg/L $Cl_2$ to mg/L $Br_2$ the determined result for "free chlorine" or "total chlorine" in terms of mg/L $Cl_2$ should be multiplied by 2.25.

While the DBDMH utilized in the practice of this invention can be in the form of a powder, granules, caplets, tablets, briquettes, or pucks, it is preferred to utilize the DBDMH in the form of granules having properties described above. A preferred process for producing highly suitable powder or particulate DBDMH and novel DBDMH products are described respectively in commonly-owned copending application Ser. Nos. 09/484,844 and 09/484,687, both filed Jan. 18, 2000. Methods for the formation of compacted forms of DBDMH such as caplets, tablets, briquettes and pucks are described in commonly-owned copending application Ser. No. 09/487,816, filed Jan. 18, 2000. Methods for producing DBDMH in granular form are described in commonly-owned copending application Ser. No. 09/483,896, filed Jan. 18, 2000. The disclosures of each of the foregoing applications are incorporated herein by reference as if fully set forth herein.

The methods of this invention thus involve use of one or more 1,3-dibromo-5,5-dialkylhydantoins (DBDAH) in binder-free or binder-containing forms, "binder" being used to denote any foreign substance added to the DBDAH to bind the particles together or otherwise increase the average hardness of an aggregate formed therefrom. In converting the 1,3-dibromo-5,5-dialkylhydantoin particulate solids, into granules, with or without a binder, conventional processing equipment can be used under the usual operating conditions. Typically, the 1,3-dibromo-5,5-dialkylhydantoinparticulate solids, are compressed into sheet form by means of a roll compactor. This sheet in turn is broken up into small granules by a mechanical device, such as a Chilsonator® breaker (The Fitzpatrick Company, Elmhurst, Ill.). The granules are then classified by screening into the desired size range. Undersized granules are typically recycled to the roll compactor, whereas oversized granules are recycled to the breaker device. When used in the form of granules without use of a binder, a preferred process involves (a) compressing 1,3-dibromo-5,5-dimethylhydantoin particulate solids in the absence of a binder into a sheet of a thickness in the range of about 1/16 inch to about 1/2 inch; (b) subdividing such sheet into particles comprising particles in the range of about 80 U.S. standard mesh size to about 3 U.S. standard mesh size, and preferably in the range of about 30 U.S. standard mesh size to about 8 U.S. standard mesh size; and (c) recovering particles from (b) in the range of about 80 U.S. standard mesh size to about 3 U.S. standard mesh size, and preferably in the range of about 30 U.S. standard mesh size to about 8 U.S. standard mesh size. The same procedure can be used in forming granules of DBDAH containing a binder. All that is further required is to mix a suitable quantity of one or more binders with the DBDAH before conducting step (a) above.

Another way of producing granules for use in the practice of this invention, involves converting the particulate DBDAH solids into mini-briquettes, which are then broken up by means of a suitable mechanical device such as a hammer mill into particles which for the most part are in the size range desired. These particles are then screened by means of a mechanical size classifier which agitates the particles on an upper coarse screen positioned above a lower screen of smaller aperture size. After conducting such classification, the particles retained on the smaller aperture screen are then subjected to a second mechanical size classification on a separator which agitates the particles on a single screen in order to reduce the sharp edges which can result in formation of fines or dust during subsequent handling. For example, the first such mechanical size classifier can be a 60-inch Sweco® Vibro-Energy® separator in which the upper coarse screen has an average sieve aperture of about 0.385 inch or 0.312 inch and in which the lower screen has an average sieve aperture of about 0.157 inch (or 5 U.S. standard mesh size). The second such separator can be a 24-inch Sweco® Vibro-Energy® separator equipped with a screen having an average sieve aperture of about 0.157 inch. Use of the foregoing procedures enables production of essentially dust-free finished granules useful in the practice of this invention. Such granules typically have an average particle size in the range of about 40 U.S. standard mesh size to about 5/16-inch, and preferably an average particle size in the range of about 40 U.S. standard mesh size to about 3/8-inch. The latter size range is preferred for the industrial water treatment applications of this invention.

DBDAH can be used in non-compacted forms (i.e., in the form of powders or small non-compressed particles. This is less preferred as the powders or particles are typically introduced into the water either by hand or by use of a dispenser that feeds the powder or particles into the water by dropping the powder or particles in suitable amounts and frequency into the water. It is not recommended to employ automatic in-line, off-line and floating dispensers with powders or small particles of DBDAH as the ability to control the rate of feeding of such materials is very difficult as the powders or small particles dissolve more rapidly than larger forms of DBDAH and also because of the flow of water into in-line and off-line automatic dispensers and the close proximity of floater type dispersers to water, the DBDAH can cake up in such dispensers.

Preferably, DBDAH is used in compacted forms. The compacted forms can be produced without use of a binder, and at least in the case of 1,3-dibromo-5,5-dimethylhydantoin, the average particle size before compaction should be at least 175 microns. Alternatively, the compacted forms can be produced with use of a binder. A preferred type of binder for producing such compacted products is a saturated, normally solid, fatty amide as described in U.S. Pat. No. 5,565,576, issued Oct. 15, 1996 to L. K. Hall, J. A. Falter, and T. E. Farina, the disclosure of which patent is incorporated herein in toto as if fully set forth herein. In the practice of this invention such fatty amide binder is preferably used with one or more 1,3-dibromo-5,5-dialkylhydantoins (DBDAH) having an average particle size of at least 175 microns, although smaller particle sized DBDAH may be used. A particularly preferred type of binder for use in producing the compacted forms of DBDAH for use in this invention is a micronized synthetic polyolefin-based hydrocarbon wax and/or a micronized synthetic polyfluorocarbon wax effective to form the compacted product, provided the wax is suitably compatible with the 1,3-dibromo-5,5-dimethylhydantoin. In the practice of this invention with compacted forms of blends of DBDAH with a micronized synthetic polyolefin-based hydrocarbon wax and/or a micronized synthetic polyfluorocarbon wax, the average particle size of the DBDAH can be in the range of about 20 to about 600 microns, but preferably the average particle size of the DBDAH is in the range of about 175 to about 400 microns, if not even greater.

Other less preferred substances that can be used for the purpose of binding the particles of DBDAH together are described, for example, in U.S. Pat. No. 4,677,130 (alkali or alkaline earth metal salts), and in Published International Application No. WO 97/15652 (borax). Still other binders may be used provided they do not interfere with the functioning of the compacted form of DBDAH.

As noted above, the 1,3-dibromo-5,5-dialkylhydantoinbiocide(s) used in the practice of this invention can be, and preferably are continuously or substantially continuously introduced by means of a dispenser into the water being treated. The 1,3-dibromo-5,5-dialkylhydantoin biocide(s) can be of various compacted forms when used in such dispensers, such as tablets, sticks, pucks, blocks, or the like. However a preferred compacted form for such use is granular form. Thus an embodiment of this invention is a dispenser that is designed and constructed to automatically release into a body of water from a supply of compacted 1,3-dibromo-5,5-dialkylhydantoin, continuously or substantially continuously, a biocidally effective amount of active bromine species. One preferred type of dispenser which, when used pursuant to this invention, can automatically dispense into the water, continuously or substantially continuously, a biocidally effective amount of active bromine species resulting from use of one or more of the 1,3-dibromo-5,5-dialkylhydantoins referred to herein in compacted form, is a floater-type dispenser. Such dispensers have sufficient buoyancy to float on the body of water with a portion of the device submerged below the water surface. Openings, typically of pre-adjustable size, are in the submerged portion so that contact between the water and the biocide within the dispenser is maintained. U.S. Pat. No. 4,241,025 describes a floater-type dispenser that may be used. A particularly preferred floater-type dispenser is the Rainbow Lifegard swimming pool floater, which is sized to hold about 3 pounds of granular product. One important aspect of this invention is the discovery that a floater-type dispenser of this type when used with granules of a 1,3-dibromo-5,5-dialkylhydantoin, viz., 1,3-dibromo-5,5-dimethylhydantoin can provide excellent microbiological control in bodies of water, especially bodies of industrial water, such as in cooling towers. These granules in the form charged into the floater-type dispenser have at least one and most preferably both of the following characteristics: (i) an average crush strength of at least about 15 pounds per inch of thickness and more preferably at least about 20 pounds per inch of thickness; and (ii) an average size in the range of about 40 U.S. standard mesh size to about ⅜-inch.

Another type of automatic dispenser which has been very successfully employed pursuant to this invention when charged with 1,3-dibromo-5,5-dimethylhydantoin granules having the above properties is described in U.S. Pat. No. 4,617,117, all disclosure of which, including specifically the drawings, the description pertaining to the drawings, and each of the 10 claims thereof, is incorporated herein by reference. A commercially-available model, Hayward model CL 200 in-line feeder (Hayward Pool Products, Inc., has been used with such granules despite instructions prevalent in the art teaching away from use of feeders of this type with anything other than the types and forms of chemical biocides specifically identified by the manufacturer of the feeder. For example, on the Feeder lid for the Hayward Model 200 Series there is a CAUTION notice which includes the following:

USE ONLY TRICHLORO-S-TRIAZINETRIONE TABLETS—SLOW DISSOLVING TYPE

Another type of automatic dispenser which has been used very successfully pursuant to this invention when charged with 1,3-dibromo-5,5-dimethylhydantoin granules having the above properties is the Rainbow Model 320 automatic chlorine/bromine in-line feeder (Pentair Pool Products, Inc., Sanford, N.C. and Moorpark, Calif.). Also suitable are the Rainbow high-capacity chlorine/bromine off-line feeders available from the same source.

Still another type of automatic dispenser which can be very successfully employed pursuant to this invention when charged with 1,3-dibromo-5,5-dimethylhydantoin granules having the above properties is described in U.S. Pat. No. 5,089,127, all disclosure of which, including specifically the drawings, the description pertaining to the drawings, and each of the 20 claims thereof, is incorporated herein by reference. A commercially-available model, corresponding to the patent is available from PPG Industries, Inc. adapted for in-line or off-line service can be used with such granules despite the fact that this feeder has been constructed to utilize solid sanitizing tablets such as the calcium hypochlorite tablets described in U.S. Pat. No. 4,865,760. In using this commercially-available feeder, one should ensure that the water flow to the feeder is increased relative to the optimal feed rate for such calcium hypochlorite tablets. This can easily be done by adjusting the setting of the inlet valve to a higher setting than used with the calcium hypochlorite tablets.

While still other commercially-available automatic in-line or off-line feeders may be used with the above granules in the practice of this invention, not all commercially-available automatic in-line or off-line feeders can be used with the above described 1,3-dibromo-5,5-dialkylhydantoin granules. For example, the feeder such as described in U.S. Pat. No. 5,076,315 was found unsuitable for use with DBDMH granules having the above properties. Thus in instances where the suitability of such dispenser or feeder has not already been established, one should perform a few preliminary tests using DBDMH granules of the above type to determine whether the device can be effectively used with such granules.

The various new features of this invention and the advantages accruing therefrom will be further apparent from Examples 1–5, which as presented for purposes of illustrating the invention without limiting the scope of the invention.

EXAMPLE 1

Simulated cooling water was prepared using deionized water to which calcium chloride and sodium bicarbonate were added to provide calcium hardness of 400 ppm and a total alkalinity of 300 ppm. A small amount of phosphonobutanetricarboxylic acid (PBTC) (5 ppm) was used to prevent calcium carbonate precipitation. Concentrated sodium hydroxide was added to adjust the pH of the simulated cooling water solutions to pH 9.1.

Stock solutions of DBDMH and of BCDMH were prepared by slurrying 1 gram of the respective powders in 100 mL of deionized water. After stirring for 20 minutes, the insolubles were filtered to yield clear saturated stock solutions of DBDMH and BCDMH, respectively. Iodometric titration of the stock solutions using the potassium iodide-sodium thiosulfate method indicated the DBDMH solution contained 580 mg/L (as total chlorine), and the BCDMH solution contained 1100 mg/L (as total chlorine).

The stock solutions were used to dose two simulated cooling water solutions to 1 mg/L as total chlorine. Thus, 1.7 mL of DBDMH stock solution was introduced to 1000 mL of simulated cooling water to form a first test solution, and 0.91 mL of BCDMH stock solution was introduced to another 1000 mL of simulated cooling water to produce a second test solution. Both of these test solutions were placed in screw-capped amber bottles to shield from light and prevent evaporation. The bottles were then placed in an oven and heated to 38° C. (100° F.). As soon as the solutions reached the equilibrium temperature of 38° C., 10 mL aliquots of each test solution were removed and analyzed using Hach Method 8167 for "total chlorine", to confirm that each contained a "total chlorine" level of 1 mg/L. The same solutions were also analyzed using Hach Method 8021 for "free chlorine" to determine how much of the total chlorine species also registered as "free chlorine". These analyses were recorded as results at time 0. The test solutions were then kept in the oven at the equilibrium temperature of 38° C. for a total of 6 hours during which time additional 10 mL aliquots were removed at known time intervals and subjected to the same analysis procedures for "free chlorine" and "total chlorine".

Figure 2:
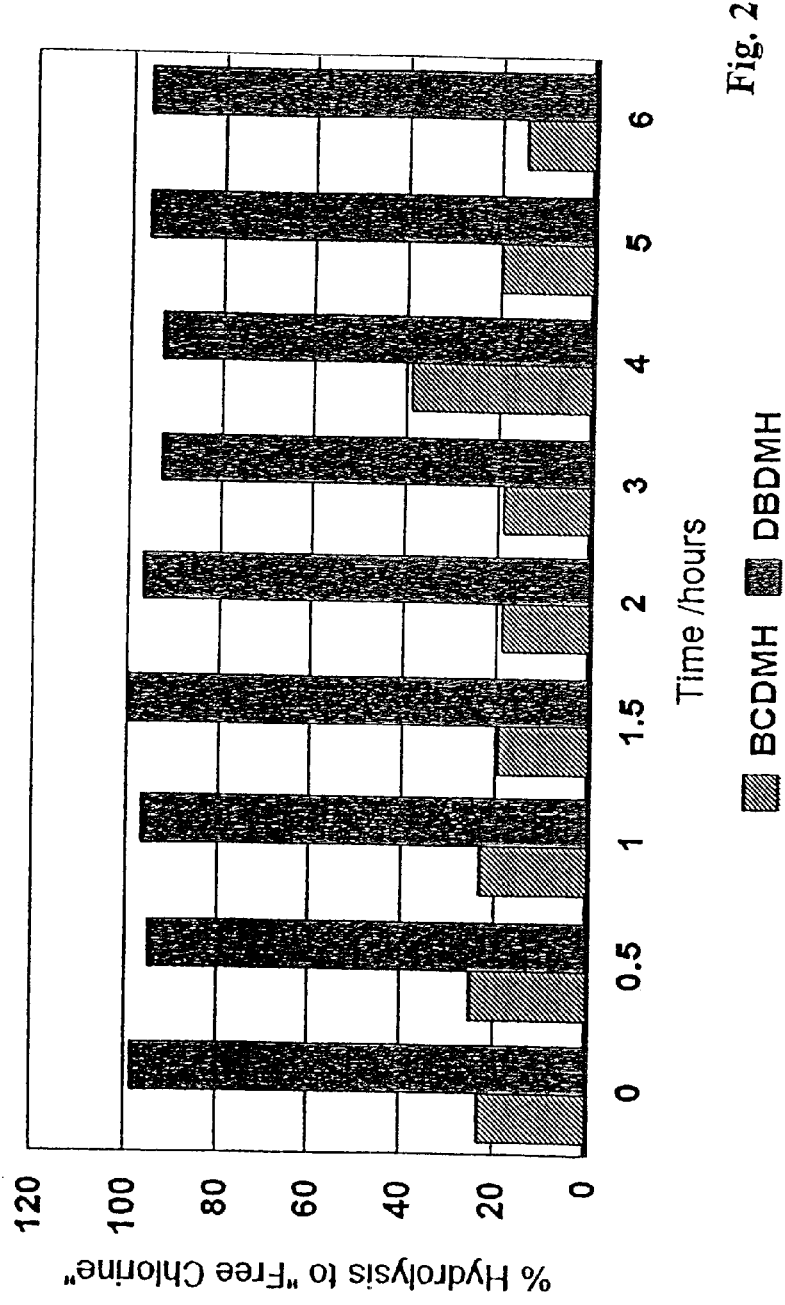
FIG. 2 is a graphical representation of the percent of hydrolysis experienced by the respective test samples of BCDMH and of DBDMH in the tests performed in Example 1.

The results of each of the foregoing determinations are summarized in Table 1 and are depicted graphically in FIG. 1. In Table 1 the values given at times 0.5 through 6 hours are percentages of the corresponding values shown in Table 1 for Time 0. These results are depicted graphically in FIG. 1. Table 2 sets forth the percentages of hydrolysis to "free chlorine" experienced by the BCDMH and the DBDMH based on the results shown in Table 1. FIG. 2 depicts the results given in Table 2. It can be seen from Table 2 and FIG.

2 that over a time span of 6 hours the differences in the percentage of hydrolysis as between BCDMH and DBDMH remained substantially constant. The minor variations in such differences appearing in Table 2 and FIG. 2 are deemed insignificant statistically inasmuch as they are within experimental error.

TABLE 1

| Time, hr | BCDMH Free Cl$_2$ | BCDMH Total Cl$_2$ | DBDMH Free Cl$_2$ | DBDMH Total Cl$_2$ |
| --- | --- | --- | --- | --- |
| 0 | 23.1 | 100 | 98.8 | 100 |
| 0.5 | 25.6 | 104 | 100 | 104 |
| 1 | 23.1 | 100 | 85.1 | 87.3 |
| 1.5 | 17.9 | 92.3 | 87.3 | 87.3 |
| 2 | 16.6 | 88.5 | 81.6 | 83.9 |
| 3 | 16.6 | 88.5 | 70.1 | 74.7 |
| 4 | 30.7 | 79.5 | 65.5 | 66.6 |
| 5 | 15.4 | 76.9 | 60.1 | 63.2 |
| 6 | 10.2 | 71 | 59.8 | 62 |

TABLE 2

| Time, hr | BCDMH % hydrolysis to Free Cl$_2$ | DBDMH % hydrolysis to Free Cl$_2$ |
| --- | --- | --- |
| 0 | 23.1 | 98.8 |
| 0.5 | 24.7 | 95.6 |
| 1 | 23.1 | 97.3 |
| 1.5 | 19.4 | 100 |
| 2 | 18.8 | 97.2 |
| 3 | 18.8 | 93.8 |
| 4 | 38.7 | 93.8 |
| 5 | 20 | 96.4 |
| 6 | 14.3 | 96.3 |

EXAMPLE 2

The effectiveness of DBDMH and of BCDMH in microbiological control in cooling tower water was investigated in comparative tests. The cooling tower consisted of two 500-ton units in a crossflow design. The total system-contained volume was 14,000 gallons, and the tower contained medium efficiency film fill. Water from the tower cooled the coils of two 300-ton air conditioners (chillers). The tower typically operated at a pH of about 9.1 and 4 cycles of concentration. Blowdown was controlled by conductivity. Make-up water consisted of softened city water and which was of good quality. The make-up water was very low in calcium (<10 mg/L) but high in pH (8.7). The alkalinity was 145 mg/L (as CaCO$_3$), and the silica level was 28 mg/L. The tower employed a conventional polyphosphate/molybdate/phosphonate program to provide corrosion and deposit control. The conditions and results are summarized in Table 3.

TABLE 3*

|  | Cooling Tower Water | Make-up Water |
| --- | --- | --- |
| Cooling Tower Data |  |  |
| Temperature (return line) | 91° F. | — |
| Temperature (to process) | 83° F. | — |
| Δ T | 8° F. | — |
| Make-up water | 4800 gal/day | — |
| Water Chemistry |  |  |
| Conductivity, mS/cm | 1.22 | 0.32 |
| pH, units | 9.2 | 8.7 |

TABLE 3*-continued

|  | Cooling Tower Water | Make-up Water |
| --- | --- | --- |
| Alkalinity, mg/L as CaCO$_3$ | 480 | 145 |
| Total Hardness, mg/L as CaCO$_3$ | 1 | 3 |
| Silica, mg/L | 100 | 28 |

*This data represents the average of several analyses conducted during the course of the field trial.

The BCDMH (20 lbs) was introduced to the water using 20-gram, 1-inch tablets charged to a solid halogen feeder (Neptune model BT-40, Neptune Chemical Pump Co., Inc., Lansdale, Pa.). Before each dose, the cooling tower water was sampled and enumerated for heterotrophic bacteria plate counts. Then the tower was slug dosed three times a week with BCDMH. Slug dosing was accomplished by diverting through the feeder containing the tablets a sidestream of the recirculating water for about 1 to 5 hours until a "free chlorine" dose of about 0.5 mg/L (as "free chlorine") was obtained. The "total chlorine" dose was measured at the same time. After each dose the cooling water was sampled and enumerated for heterotrophic bacteria plate counts. As necessary, the feeder was replenished with more BCDMH tablets. The total dry weight of BCDMH tablets consumed over a 30-day test period (obtained by subtracting the dry weight of the tablets remaining in the feeder at the completion of the test from the total dry weight of the tablets added to the feeder during the test period) was found to be 25 lbs.

It was found that this biocide program (biocide dose 0.5 mg/L "free chlorine") reduced heterotrophic bacterial levels in the bulk water by an average of 1 order of magnitude. For example, before the biocide dose the bacteria levels in the bulk water ranged from $10^5$ to $10^4$ CFUs/mL. After the biocide dose the bacteria levels in the bulk water were reduced to $10^4$ to $10^3$.

After emptying the feeder of BCDMH tablets, 20 lbs of DBDMH granules was charged into the feeder. Thereupon the same procedure as described above for the BCDMH was carried out except for the fact that is was unnecessary to add any additional DBDMH to the feeder during the 30-day test period. In fact, the total weight of DBDMH consumed during the test was only 7 lbs. Also, the targeted 0.5 mg/L "free chlorine" dose in the bulk water was achieved in only 20 to 30 minutes. It was found that the biocidal performance provided by 7 lbs of DBDMH was the same as provided by 25 lbs of BCDMH under the same test conditions.

A summary of these comparative experiments is presented in Table 4.

TABLE 4

|  | BCDMH Tablets | DBDMH Granules |
| --- | --- | --- |
| Slug Dose Program | 3 times/week | 3 times/week |
| Feed Time | 1–5 hrs. | <0.5 hrs. |
| Halogen residual as free Cl$_2$ | 0.5 ppm | 0.5 ppm |
| Consumption rate | 25 lbs/month | 7 lbs/month |
| Bacteria reduction | 1.5–2 logs | 1.5–2 logs |
| Mild steel corrosion | 0.75 mpy | 0.21 mpy |
| Copper corrosion | 0.34 mpy | 0.13 mpy |

EXAMPLE 3

Using the same cooling tower as used in Example 2, the effectiveness of 1,3-dibromo-5,5-dimethylhydantoin in microbiological control in cooling tower water was investigated. As noted above, the cooling tower consisted of two 500-ton units in a crossflow design. The total system-contained volume was 14,000 gallons, and the tower contained medium efficiency film fill. Water from the tower cooled the coils of two 300-ton air conditioners (chillers). The tower typically operated at a pH of about 9.1 and 4 cycles of concentration. Blowdown was controlled by conductivity. Make-up water consisted of softened city water and which was of good quality. The make-up water was very low in calcium (<10 mg/L) but high in pH (8.7). The alkalinity was 145 mg/L (as $CaCO_3$), and the silica level was 28 mg/L. The tower employed a conventional polyphosphate/molybdate/phosphonate program to provide corrosion and deposit control.

The 1,3-dibromo-5,5-dimethylhydantoin was introduced to the water using granules charged to a solid halogen feeder (Neptune model BT-40, Neptune Chemical Pump Co., Inc., Lansdale, Pa.). The field trial lasted 51 days. The tower was slug dosed three times a week with 1,3-dibromo-5,5-dimethylhydantoin. Slug dosing was accomplished by diverting a sidestream of the recirculating water through the feeder containing the granules for about 1 to 5 hours until a total halogen residual of about 0.75 mg/L (as $Cl_2$) was obtained. This biocide program reduced bacterial levels in the bulk water by an average of 2 orders of magnitude, with bacteria levels in the bulk water after the biocide dose ranging from $10^1$ to $10^3$ CFUs/mL.

The results from the average of several analyses conducted during the course of this field trial using DBDMH were as follows: In the microbiological tests, the levels of aerobic bacteria were in the range of $6\times10^0$ to $3\times10^3$ CFUs/mL in the cooling tower water and $10^0$ in the make-up water. As regards water chemistry, the free halogen residual (as $Cl_2$) was 0.79 mg/L (the range being 1.9–0.00 mg/L) in the cooling tower water and 0.05 mg/L in the make-up water; and the total halogen residual (as $Cl_2$) was 0.82 mg/L (the range being 1.9–0.03 mg/L) in the cooling tower water and 0.8 mg/L in the make-up water.

EXAMPLE 4

A field test was conducted at a HVAC/process cooling system averaging 400–500 tons in each of four cooling cells. In this system 90% of the heat load to the water was through the HVAC system and the remaining 10% heat load to the water was through process cooling of chemical reactors. The total capacity of the system was 16,000 gallons and involved a temperature differential of about 7–8° F. The operating pH of the system was in the range of 8.3 to 8.8. The water contained 900–1000 ppm of total dissolved solids and had a calcium hardness of 270–300 ppm. Operation involved approximately three cycles of concentration.

This installation had been employing BCDMH briquettes. At the beginning of this field test it was noted that the installation had very poor water flow because the system was choked with considerable amounts of biofilm slime. The field test involved switching the biocide to granules of DBDMH. Otherwise the operation was conducted as before. The results of the 2-month field test and a summary of the available information on the prior usage in the system of BCDMH are summarized in Table 5.

TABLE 5

|  | BCDMH | DBDMH |
| --- | --- | --- |
| Slug dose Program | 6–7 times/week | 5 times/week |
| Feed time | 5–8 hours | 0.5 hour |
| Halogen residual as free $Cl_2$ | <0.3 ppm | >1.0 ppm |
| Consumption rate | 75–87 lbs/week | 28 lbs/week |
| Typical ORP, mV | 400–500 | 500–600 |
| Mild steel corrosion | data not available | 0.49 mpy |
| Copper corrosion | data not available | 0.09 mpy |

EXAMPLE 5

Another field test was carried out in the cooling tower described in Example 2 above. In this field test the cooling tower water was substantially continuously dosed with DBDMH using a Rainbow Lifeguard swimming pool floater having a capacity of about 3 lbs of granules, with the slots in the wide open position. This floater, charged with DBDMH granules, was placed and secured in the tower basin, a very convenient location for addition of the biocide when needed. The floater delivered a dose of "free halogen" to maintain a dosage level in the range of 0.15 to 0.2 ppm of free halogen as $Br_2$. It was found that the planktonic plate counts were less than $10^4$ CFU/mL and that the consumption of DBDMH was only 6 pounds per month.

The granules of DBDMH used in Examples 2–5 have an average size in the range of about 40 U.S. standard mesh size to about ⅜-inch, and an average crush strength of at least 15 pounds per inch of thickness. The combination of the low water solubility of DBDMH coupled with its use in granular form provided a slow but continuous or substantially continuous automatic dosing of the cooling tower water so that a biocidally effective level of free bromine was maintained in the water during the entire test, with relatively infrequent refilling of the dispenser being required.

It can be seen from Examples 1–5 that among the advantages of this invention are that DBDMH contains almost twice as much available bromine as BCDMH, is totally chlorine-free, and almost all of the halogen released to the water by DBDMH responds as "free chlorine" in the DPD test, this being the biocidally-effective species in the water. In addition, the practice of this invention enabled, as compared to BCDMH, (a) substantial reduction in biocide consumption, (b) significant reductions in feed time, (c) significant reductions in mild steel corrosion and in copper corrosion, (d) highly effective biocidal action against extensive biofilm infestations, (e) greatly improved performance and cleanliness in a cooling tower facility that had not been treated with biocide pursuant to this invention, and (f) highly cost-effective continuous or substantially continuous dosing of DBDMH granules into an industrial water system using an inexpensive floater type biocide dispenser.

The most effective presently-known process for producing 1,3-dibromo-5,5-dimethylhydantoin for use in the practice of this invention is described in commonly-owned copending application Ser. No. 09/484,844, filed Jan. 18, 2000. That process comprises, for example, concurrently feeding (i) an aqueous solution or slurry formed from an inorganic base and 5,5-dimethylhydantoin, and (ii) a brominating agent in proportions such that each nitrogen atom is substituted by a bromine atom, thereby continuously forming product which precipitates in an aqueous reaction mixture. The pH of the mixture is continuously maintained in the range of about 5.5 to about 8.5. Examples 6–16 below illustrate that process. In Examples 6–16, pH was monitored by use of a pH meter. In Examples 6–15, bromine was fed using a Cole-Parmer Masterflex computerized drive and Easy-Load® pump head. When conducting the continuous operations of Examples 14 and 15, the resulting reaction slurry was collected manually and intermittently from the bottom of the reactor. Each fraction was collected in a 500 mL flask.

EXAMPLE 6

235 Grams of NaOH (5.85 mol) are dissolved in 1800 g of water, and 375 g of 5,5-dimethylhydantoin (2.93 mol) is added to the NaOH solution. There are 935 g of $Br_2$ (5.85 mol) in the bromine reservoir. A 1-liter jacketed flask into which the $Br_2$ and the 5,5-dimethylhydantoin/NaOH solution are fed is maintained at 25° C. with a cooling bath. The 5,5-dimethylhydantoin/NaOH solution is co-fed to the reaction flask simultaneously with, but separately from, $Br_2$. The feed of the 5,5-dimethylhydantoin/NaOH solution was initiated shortly before (e.g., 3–4 min.) the initiation of the $Br_2$ feed. The feed rate of the 5,5-dimethylhydantoin/NaOH solution is 10 mL/minute, and the feed rate of the $Br_2$ is 1.60–1.70 mL/minute. The reaction mixture is stirred with a mechanical stirrer at a rate of 350–400 rpm. During the reaction, the pH ranged from 7.4 to 7.9. The slurry that forms as the reaction progresses is collected at a rate such that the level of the solution in the reaction flask remains constant. 500 mL fractions of product are collected through the bottom of the reaction flask, in an average time of 30 minutes per fraction. When the 5,5-dimethylhydantoin/NaOH solution feed is finished, 86 g of $Br_2$ (0.54 mol) remains in the bromine reservoir.

Each product fraction is filtered and washed with three 500 mL portions of water, and the solid is then dried under a stream of nitrogen. The isolated yield of 1,3-dibromo-5,5-dimethylhydantoin is 673 g, a yield of 80% based on 5,5-dimethylhydantoin, or a yield of 89% based on $Br_2$. The active bromine content is at least 99%, as determined by iodometric titration.

EXAMPLE 7

44 Grams of NaOH (1.1 mol) are dissolved in 338 g of water, and 70.4 g of 5,5-dimethylhydantoin (0.55 mol) is added to the NaOH solution. There are 175.1 g of $Br_2$ (1.1 mol) in the bromine reservoir. The reaction flask into which the $Br_2$ and the 5,5-dimethylhydantoin/NaOH solution are fed is maintained at 35° C. with a heating bath. The reaction flask is charged with ~200 mL heel (238 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.9 to 8.0. The reaction temperature stabilized at 37° C. during the 0.5 hour addition time. When the addition of reagents is finished, the orange slurry is filtered at 35° C. and washed with 650 mL of water. The resultant white solid is dried overnight under a stream of nitrogen. The isolated yield of 1,3-dibromo-5,5-dimethylhydantoin is 147.6 g, a yield of 94%, and the active bromine content of the 1,3-dibromo-5,5-dimethylhydantoin is 55.1 wt % (98.6% of the theoretical value), as determined by iodometric titration.

EXAMPLE 8

44 Grams of NaOH (1.1 mol) are dissolved in 338 g of water, and 70.4 g of 5,5-dimethylhydantoin (0.55 mol) is added to the NaOH solution. There are 172.0 g of $Br_2$ (1.07 mol) in the bromine reservoir. The reaction flask into which the $Br_2$ and the 5,5-dimethylhydantoin/NaOH solution are fed is maintained at 67° C. with a heating bath. The reaction flask is charged with ~200 mL heel (238 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The bromine is diluted with nitrogen and fed below the surface of the solution in the reaction flask. The reaction mixture is stirred with a mechanical stirrer at a rate of 400 rpm; the pH ranged from 6.7 to 7.1 during the reaction. During the 0.5 hour addition time, the reaction temperature stabilized at 67° C. When the addition of reagents is finished, the orange slurry is discharged from the reaction flask into a beaker and allowed to cool slowly. The slurry is filtered at ~45° C. and washed with two 500 mL portions of water. The resultant white solid is dried overnight under a stream of nitrogen. The isolated yield of 1,3-dibromo-5,5-dimethylhydantoin is 130.5 g, a yield of 83% based on 5,5-dimethylhydantoin, or a yield of ~85% based on $Br_2$. The active bromine content of the 1,3-dibromo-5,5-dimethylhydantoin is 55.9 wt % (100% of the theoretical value), as determined by iodometric titration. Particle size data on the 1,3-dibromo-5,5-dimethylhydantoin product formed in this operation based on a representative dried sample of the product are summarized in Table 6.

TABLE 6

| Particle Size Category | Particle Size of Product |
| --- | --- |
| Average | 237.5μ |
| 10% is greater than | 371.6μ |
| 25% is greater than | 309.8μ |
| 50% is greater than | 239.1μ |
| 75% is greater than | 165.6μ |
| 90% is greater than | 99.81μ |
| Range | 0.040–541.9μ |

EXAMPLE 9

354 Grams of NAOH (8.85 mol) are dissolved in 2700 g of water. 562 g of 5,5-dimethylhydantoin (4.386 mol) is added to the NaOH solution. The reaction flask is charged with 500 mL heel of a 1,3-dibromo-5,5-dimethylhydantoin filtrate (mother liquor). The 5,5-dimethylhydantoin/NaOH solution is co-fed to the jacketed reaction flask, no heating or cooling is applied simultaneously with, but separately from, $Br_2$. The feed rate of the 5,5-dimethylhydantoin/NaOH solution is 10 mL/minute, and the feed rate of the $Br_2$ is initially 1.70 mL/minute, but is adjusted later to 1.68 mL/minute to maintain the pH of the reaction mixture at ~7.0. The reaction mixture is stirred with a mechanical stirrer at a rate of 400 rpm reaction temperature is stabilized at about 42° C. The slurry that forms as the reaction progresses is collected at a rate such that the level of the solution in the reaction flask remains constant. Eight 500 mL fractions of product were collected through the bottom of the reaction flask, in an average time of 30 minutes per fraction. A total of 1374.5 g of $Br_2$ (8.59 mol) are added during the reaction.

Each product fraction is filtered and washed with a 500 mL portion of water; the solids are then dried overnight at 50° C. in a vacuum oven. The total isolated yield of 1,3-dibromo-5,5-dimethylhydantoin is 1152 g, a yield of 92% based on 5,5-dimethylhydantoin, or a yield of 94% based on $Br_2$. The active bromine content of the 1,3-dibromo-5,5-dimethylhydantoin ranges from 55.4 wt % to 55.7 wt % (99.1% to 99.7% of the theoretical value), as determined by iodometric titration. The average particle size of the 1,3-dibromo-5,5-dimethylhydantoin is greater than 150μ.

EXAMPLE 10

89 Grams of NaOH (2.2 mol) are dissolved in 676 g of water, and 141 g of 5,5-dimethylhydantoin (1.1 mol) is added to the NaOH solution. There are 350 g of $Br_2$ (2.2 mol) in the bromine reservoir. The reaction flask into which the $Br_2$ and the 5,5-dimethylhydantoin/NaOH solution are fed is maintained at 67° C. with a heating bath. The reaction flask is charged with ~400 mL heel (483 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.1. The reaction temperature stabilized at 67° C. during the 66 minute addition time. When the addition of reagents is finished, the orange slurry is filtered at 43° C. and washed with 1000 mL (2×500 mL) of water. The resultant white solid is dried overnight under a stream of nitrogen. 307.3 Grams of $Br_2$ (1.92 mol) had been fed to the reaction flask. The isolated yield of 1,3-dibromo-5,5-dimethylhydantoin is 212.5 g, a yield of 77% based on $Br_2$, and 68% based on 5,5-dimethylhydantoin; the active bromine content of the 1,3-dibromo-5,5-dimethylhydantoin is 55.9 wt % (100% of the theoretical value), as determined by iodometric titration.

EXAMPLE 11

88 Grams of NaOH (2.2 mol) are dissolved in 338 g of water, and 140.8 g of 5,5-dimethylhydantoin (1.1 mol) is added to the NaOH solution. There are 352 g of $Br_2$ (2.2 mol) in the bromine reservoir. The reaction flask into which the $Br_2$ and the 5,5-dimethylhydantoin/NaOH solution are fed is maintained at 69° C. with a heating bath. The reaction flask is charged with ~200 mL heel (240 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.0. The reaction temperature stabilized at 68–69° C. during the 39 minute addition time. When the addition of reagents is finished, the orange slurry is filtered at 40° C. and washed with 500 mL of water. The resultant white solid is dried overnight under a stream of nitrogen. 285.5 Grams of $Br_2$ (1.78 mol) had been fed to the reaction flask. The isolated yield of 1,3-dibromo-5,5-dimethylhydantoin is 186.8 g, a yield of 73% based on $Br_2$, and 60% based on 5,5-dimethylhydantoin; the active bromine content of the 1,3-dibromo-5,5-dimethylhydantoin is 53.4 wt % (96% of the theoretical value), as determined by iodometric titration.

Table 7 summarizes the particle size data for the products of Examples 10 and 11.

TABLE 7

| Particle Size Category | Particle Size of Product - Example 10 | Particle Size of Product - Example 11 |
| --- | --- | --- |
| Average | 210.4μ | 293.6μ |
| 10% is greater than | 381.7μ | 451.2μ |
| 25% is greater than | 298.3μ | 349.6μ |
| 50% is greater than | 196.8μ | 256.3μ |
| 75% is greater than | 115.3μ | 174.9μ |
| 90% is greater than | 56.86μ | 110.6μ |
| Range | 0.040–594.9μ | 0.040->2000μ |

EXAMPLE 12

44.2 Grams of NaOH (1.1 mol) are dissolved in 338 g of water, and 70.4 g of 5,5-dimethylhydantoin (0.55 mol) is added to the NaOH solution. There are 173 g of $Br_2$ (1.08 mol) in the bromine reservoir. The reaction flask into which the $Br_2$ and the 5,5-dimethylhydantoin/NaOH solution are fed is maintained at 57° C. with a heating bath. The reaction flask is charged with 200 mL heel (244 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 57° C. during the 33 minute addition time. When the addition of reagents is finished, the orange slurry is filtered at 38° C. and washed with 500 mL of water. The resultant white solid is dried overnight under a stream of nitrogen. The isolated yield of 1,3-dibromo-5,5-dimethylhydantoin is 139.8 g, a yield of 91% based on $Br_2$, and 89% based on 5,5-dimethylhydantoin; the active bromine content of the 1,3-dibromo-5,5-dimethylhydantoin is 55.7 wt % (99.7% of the theoretical value), as determined by iodometric titration.

EXAMPLE 13

44.2 Grams of NaOH (1.1 mol) are dissolved in 338 g of water, and 70.3 g of 5,5-dimethylhydantoin (0.55 mol) is added to the NaOH solution. There are 172.5 g of $Br_2$ (1.08 mol) in the bromine reservoir. The reaction flask into which the $Br_2$ and the 5,5-dimethylhydantoin/NaOH solution are fed is maintained at 48° C. with a heating bath. The reaction flask is charged with ~200 mL heel of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 48° C. during the 34 minute addition time. When the addition of reagents is finished, the orange slurry is filtered at 38° C. and washed with 500 mL of water. The resultant white solid is dried overnight under a stream of nitrogen. The isolated yield of 1,3-dibromo-5,5-dimethylhydantoin is 144.8 g, a yield of 94% based on $Br_2$, and 92% based on 5,5-dimethylhydantoin; the active bromine content of the 1,3-dibromo-5,5-dimethyl-hydantoin is 55.0 wt % (98.4% of the theoretical value), as determined by iodometric titration.

The particle size data for the products of Examples 12 and 13 are summarized in Table 8.

TABLE 8

| Particle Size Category | Particle Size of Product - Example 12 | Particle Size of Product - Example 13 |
|---|---|---|
| Average | 231.2μ | 178.4μ |
| 10% is greater than | 338.3μ | 281.1μ |
| 25% is greater than | 285.0μ | 230.9μ |
| 50% is greater than | 228.8μ | 175.7μ |
| 75% is greater than | 177.8μ | 125.0μ |
| 90% is greater than | 133.0μ | 79.14μ |
| Range | 0.040–493.6μ | 0.040–409.6μ |

EXAMPLE 14

The process of this Example was conducted in a continuous fashion. A feed solution of 5,5-dimethylhydantoin/NaOH was formed by adding 5,5-dimethylhydantoin to a 9 wt % NaOH solution, such that the 5,5-dimethylhydantoin concentration was about 1.1 M. The 5,5-dimethylhydantoin/NaOH solution was co-fed to the reaction flask simultaneously with, but separately from, $Br_2$. The flask was suspended in a heating bath. The reaction mixture was stirred with a mechanical stirrer at a rate of 500 rpm. The reaction mixture was maintained at a pH of about 7.0±0.2, and the reaction temperature was maintained at 55° C. Ten fractions of product were collected in an average time of 30 minutes per fraction. The isolated yield of the 1,3-dibromo-5,5-dimethylhydantoin was 90% based on 5,5-dimethylhydantoin, and 92% based on added $Br_2$. The purity of the 1,3-dibromo-5,5-dimethylhydantoin, a white crystalline product, was 99.8%, based on the theoretical bromine content. Fractions 5–10 represent the particle size of the product as formed during steady-state operating conditions. Table 9 summarizes average particle size data and particle size distribution data relating to fractions 5–10 based on samples of each such fraction taken during the steady-state operation of the continuous process. The determinations showed that a bimodal distribution of the product had been produced. The overall average particle size of the product was 512.3 microns.

TABLE 9

| Particle Size | Fraction 5 | Fraction 6 | Fraction 7 | Fraction 8 | Fractions 9 + 10 |
|---|---|---|---|---|---|
| Average | 371.7μ | 445.6μ | 535.5μ | 560.3μ | 545.9μ |
| 10% is greater than | 530.7μ | 626.0μ | 724.7μ | 805.0μ | 952.1μ |
| 25% is greater than | 462.2μ | 550.9μ | 643.3μ | 729.3μ | 833.4μ |
| 50% is greater than | 386.0μ | 474.5μ | 559.7μ | 641.8μ | 676.7μ |
| 75% is greater than | 256.8μ | 369.6μ | 447.8μ | 436.1μ | 149.6μ |
| 90% is greater than | 94.76μ | 134.4μ | 150.3μ | 94.5μ | 76.02μ |
| Range | 0.791–786.9μ; 1255–1512μ | 4.241–786.9μ; 1143–1255μ | 3.519–863.9μ; 1143–1512μ | 3.519–8.639μ; 1143–1512μ | 0.721–409.6μ; 493.6–1255μ |

EXAMPLE 15

Another continuous operation was conducted in a manner similar to that of Example 14. The feed solution was formed by dissolving 355 g (8.87 mols) in 3550 g of water. To this was added 560 g (4.37 mols) of 5,5-dimethylhydantoin. The concurrent feeds were adjusted to maintain the pH of the aqueous reaction mixture at 7.0±0.2. The temperature was maintained at 55° C. The total amount of bromine ($Br_2$) fed was 1359.4 g (8.50 mols). As in Example 14, ten fractions of the reaction mixture were collected. However, in this operation, the addition rates were adjusted such that the average residence time was approximately 1 hour per fraction. The total isolated yield of 1,3-dibromo-5,5-dimethylhydantoin was 88% based on 5,5-dimethylhydantoin used and 90% based on the added bromine. The 1,3-dibromo-5,5-dimethylhydantoin product was obtained as a white crystalline solid. Table 10 summarizes the average particle size data and product distribution data relating to the product formed in this reaction. Fractions 5–10 represent the particle size of the product as formed during steady-state operating conditions. As in Example 14, the product formed was bimodal. In Table 10 "n.d." indicates that the particle size determination for the larger particle sized fraction was not determined; the instrument used could not measure particles having a particle size greater than 2000 microns. The overall average particle size of the product was at least 455.5 microns.

TABLE 10

| Particle Size | Fraction 5 | Fraction 6 | Fraction 7 | Fraction 8 | Fractions 9 + 10 |
|---|---|---|---|---|---|
| Average | 421.2μ | 478.6μ | 494.0μ | 536.6μ | 631.9μ |
| 10% is greater than | 606.5μ | 699.1μ | 781.7μ | 1063μ | 1438μ |
| 25% is greater than | 532.1μ | 623.4μ | 681.5μ | 813.9μ | 995.7μ |
| 50% is greater than | 452.3μ | 535.0μ | 548.5μ | 546.7μ | 522.8 |
| 75% is greater than | 340.0μ | 372.2μ | 176.6μ | 150.3μ | 160.7μ |
| 90% is greater than | 140.8μ | 112.8μ | 68.94μ | 72.93 | 81.68μ |
| Range | 2.423–786.9μ; n.d. | 2.423–863.9μ; n.d. | 1.520–863.9μ; 1255–1512μ | 0.04–2000μ; n.d. | 0.04–>2000μ; n.d. |

EXAMPLE 16

Another continuous operation was performed using a glass reactor into which were concurrently fed, on a continuous basis, an aqueous solution formed from 5,5-dimethylhydantoin and NaOH, and a separate feed of bromine. The aqueous solution was made by adding 5,5-dimethylhydantoin to an aqueous 9 wt % NaOH solution. This solution contained about 22.4 wt % of 5,5-dimethylhydantoin and 7 wt % NaOH. A one liter, jacketed reactor having an interior diameter of 82 millimeters equipped with an anchor agitator, with an outer diameter of 72 millimeters, was used, and a silicone fluid (Rhodersil 4720V20 fluid; Rhone-Poulenc) was circulated through the jacketing. The temperature of the reaction was controlled at 38° C. Both feeds were controlled by pumps; the average feed rate of the 5,5-dimethylhydantoin/NaOH solution was 15.84 grams/minute via a Prominent Gamma G/4A positive displacement pump, and the average feed rate of the bromine was 4.67 grams/minute via a Masterflex Easy-Load peristaltic pump. The reaction mixture was stirred at 400 rpm. The pH of the reaction was monitored by measuring the pH of the effluent using a pH meter, and the pH ranged from 6.06 to 6.36 during the reaction. Product removal from the reactor was also controlled by a pump. Residence time was, on average, 30 minutes per fraction; each fraction was about 500 mL. A yield of 90.5% of 1,3-dibromo-5,5-dimethylhydantoin was obtained, based on the amount of 5,5-dimethylhydantoin fed to the reactor. The active bromine content of the 1,3-dibromo-5,5-dimethylhydantoin was >55.3%, as determined by standard iodometric titration. Thus, the purity of this product was greater than 99.0%.

Table 11 summarizes particle size data on the 1,3-dibromo-5,5-dimethylhydantoin product formed in the continuous operation of Example 16. These data are averaged data based on two samples taken at different times during the continuous operation once steady state conditions, or essentially steady state conditions, had been achieved.

TABLE 11

| Particle Size Category | Particle Size of Product |
|---|---|
| Average | 188.9μ |
| 10% is greater than | 295.2μ |
| 25% is greater than | 255.6μ |
| 50% is greater than | 203.1μ |
| 75% is greater than | 122.5μ |
| 90% is greater than | 55.9μ |
| Range | 0.872–356.5μ |

Examples 17 and 18 illustrate methods of producing tablets from large average particle size 1,3-dibromo-5,5-dimethylhydantoin without use of binders, and the exceptional crush strength of such binder-free tablets. Example 19 illustrates the excellent flowability characteristics and low-dusting properties possessed by the large average particle size 1,3-dibromo-5,5-dimethylhydantoin.

EXAMPLE 17

Five gram samples of 1,3-dibromo-5,5-dimethylhydantoin produced by the process referred to above were compacted without binder in a Sintech® press (MTS Systems Corporation, Edenprairie, Minn.) equipped with a punch and die fabricated from Hastelloy® C alloy. Prior to filling the die, the interior surfaces of the die were lightly dusted with a micronized polypropylene wax (MICROPRO 400 wax; Micro Powders, Incorporated, Tarrytown, N.Y.) to serve as a lubricant. The pressure applied was 5000 psi with no dwell time, i.e., the pressure was automatically terminated immediately upon reaching 5000 psi. The resultant tablets after removal from the die were aged for 6 days at room temperature. Thereupon the tablets were subjected to crush strength testing utilizing a Sintech® 1/S compression apparatus (MTS Systems Corporation, Edenprairie, Minn.) equipped with Testworks software, which software is installed in the 1/S compression apparatus as supplied by MTS Systems Corporation. The apparatus includes a horizontal circular-shaped load cell interfaced with a computer, a digital micrometer also interfaced with the computer, and a vertical screw-driven piston that is disposed above the load cell and adapted to apply a downward force perpendicular to the load cell. The procedure for measuring crush strength involves measuring the thickness of the tablet with the micrometer to provide a digitized input to the computer. Next the tablet is placed on its edge on the load cell with the piston in contact with the upper edge of the tablet. Then the apparatus is activated whereby the piston commences applying a progressively increasing downward diametral force to the tablet. At the same time, the load cell continuously measures the downward force being applied to the tablet, and the input of such measurements is transmitted to the computer. When the force being applied reaches the point where the amount of force suddenly decreases to 10% of the immediately preceding force, the tablet has reached the breaking point, and the application of the force is immediately terminated by the software program. From the inputs to the computer, two values are provided, namely the pounds of force at the breaking point of the tablet, and the pounds of force per inch thickness of the tablet at the breaking point. Thus the greater the force applied, the greater the strength. Two groups of such tests were conducted. One set (Set A) involved forming and evaluating 5 tablets from a batch of 1,3-dibromo-5,5-dimethylhydantoin of large average particle size produced in a continuous process (see Examples 13 and 14). The other set (Set B) of tests involved 3 tablets produced from another batch of 1,3-dibromo-5,5-dimethylhydantoin of large average particle size produced in a batch process (see Examples 9 and 11). Table 12 summarizes the results of these tests.

TABLE 12

| Test Set | Tablet Thickness | Crush Strength | Crush Strength |
|---|---|---|---|
| A | 0.365 in. | 20.9 lb. | 57.3 lb./in. |
| A | 0.367 in. | 25.5 lb. | 69.5 lb./in. |
| A | 0.366 in. | 19.2 lb. | 52.5 lb./in. |
| A | 0.367 in. | 22.8 lb. | 62.1 lb./in. |
| A | 0.364 in. | 23.7 lb. | 65.0 lb./in. |
| Avg. of A | — | 22.4 lb. | 61.3 lb./in. |
| B | 0.353 in. | 10.7 lb. | 30.4 lb./in. |
| B | 0.352 in. | 12.8 lb. | 36.4 lb./in. |
| B | 0.354 in. | 9.8 lb. | 27.8 lb./in. |
| Avg. of B | — | 11.1 lb. | 31.5 1b./in. |

Tablets of conventional, small particle sized 1,3-dibromo-5,5-dimethylhydantoin devoid of binder cannot be tableted in the manner described above.

EXAMPLE 18

The crush strength of tablets formed from 1,3-dibromo-5,5-dimethylhydantoin formulated with a binder was illustrated in a group oftests conducted as described in Example 17. The procedure for producing the tablets was as follows: 1,3-dibromo-5,5-dimethylhydantoin having an average particle size of 189 microns was hand-mixed with 3% by weight of micronized polyethylene wax from Micro Powders Incorporated, Tarrytown, N.Y. for approximately 30 minutes. The resultant formulation was then converted into tablets as described in Example 17. The results of the crush strength tests, conducted as described in Example 17, are summarized in Table 13.

TABLE 13

| Tablet Thickness | Crush Strength | Crush Strength |
|---|---|---|
| 0.372 in. | 39.8 lb. | 107.2 lb./in. |
| 0.375 in. | 44.9 lb. | 119.9 lb./in. |
| 0.375 in. | 37.5 lb. | 100.0 lb./in. |
| 0.375 in. | 36.1 lb. | 96.5 lb./in. |
| 0.377 in. | 37.6 lb. | 99.7 lb./in. |
| Averaged Results | 39.2 lb. | 104.6 lb./in. |

EXAMPLE 19

Comparative flowability tests were carried out using a sample of 1,3-dibromo-5,5-dimethylhydantoin and samples of commercially-available 1,3-dihalo-5,5-dimethylhydantoin products. These tests involved filling an 8-ounce glass jar to about one-third of its capacity with the sample to be tested. After closing the jar, it was slowly rotated while on its side in a single direction while observing the characteristics of the contents. Table 14 summarizes the observations made in these flowability tests. In Table 14 the following abbreviations are used:

DBDMH is 1,3-dibromo-5,5-dimethylhydantoin

DCDMH is 1,3-dichloro-5,5-dimethylhydantoin

BCDMH is N,N'-bromochloro-5,5-dimethylhydantoin

TABLE 14

| N,N'-dihalohydantoin | Average Particle Size | Source | Product Characteristics |
|---|---|---|---|
| DCDMH | 108.1 microns | Aldrich Chemical Co. | Bridging occurred; high dusting, non-free-flowing powder |
| BCDMH | 323.8 microns | Aldrich Chemical Co. | Bridging occurred; high dusting, non-free-flowing powder |
| DBDMH | 162.1 microns | Aldrich Chemical Co. | Bridging occurred; high dusting, non-free-flowing powder |
| DBDMH | 64.5 microns | Albemarle Corporation | Bridging occurred; high dusting, non-free-flowing powder |
| DBDMH | 45.2 microns | Great Lakes Chemical Corporation | Bridging occurred; high dusting, non-free-flowing powder |
| DBDMH | 293.6 microns | The new process of application Ser. No. 09/484,844 | No bridging occurred; low dusting, free-flowing powder |

Examples 20–28 illustrate the preparation and properties of compacted products formed from 1,3-dibromo-5,5-dimethylhydantoin utilizing novel binders as described in commonly-owned copending application Ser. No. 09/487,816, filed Jan. 18, 2000.

EXAMPLE 20

2.5 Grams of a micronized polyethylene wax (MPP-61 1, Micro Powders Inc., Tarrytown, N.Y.), was weighed into a crystallizing dish, followed by 1,3-dibromo-5,5- dimethylhydantoin (47.5 g). A broad-bladed spatula was used to blend the mixture rather like a cook might blend butter into flour. After 10 minutes of hand mixing in this fashion, the product was admitted to a glass bottle which was rolled to assess the flowability of the mixture. The flow properties were improved over the properties of the 1,3-dibromo-5,5-dimethylhydantoin used to make the blend.

EXAMPLE 21

2.5 Grams of polypropylene wax (MICROPRO 400, Micro Powders Inc., Tarrytown, N.Y.), was weighed into a crystallizing dish, followed by 1,3-dibromo-5,5-dimethylhydantoin (47.5 g). This mixture was blended as described in Example 18, and transferred to a glass bottle which was rolled to assess the flowability of the blend. Its flow properties were improved over the properties of the 1,3-dibromo-5,5-dimethylhydantoin used to make the blend.

EXAMPLE 22

The 1,3-dibromo-5,5-dimethylhydantoin blends prepared in Examples 20 and 21 were subjected to a compaction test. Each sample was weighed, and introduced into a 0.71 inch diameter die made from Hastelloy C alloy and compacted with a screw-driven punch, also made of Hastelloy® C alloy, to a pre-set pressure. Before filling the die, its interior surfaces were lightly dusted with micronized polypropylene wax to serve as a lubricant. There was no dwell time upon attaining the compaction pressure (the pressure was released immediately). Upon extracting the tablet from the die, the thickness of the tablet was measured with a micrometer, and a visual observation of the tablet was made.

For comparison, the blends were compared to unblended, virgin, commercially produced 1,3-dibromo-5,5-dimethylhydantoin powder with an average particle size of about 64.5μ, and a commercial toilet bowl product (abbreviated in Table 15 as CTB product), which is known to be a mixture of other halogenated hydantoin compounds. This toilet bowl puck was purchased from a supermarket and ground to a powder with a mortar and pestle, and recompacted as above described.

Table 15 lists the experimental conditions and the observations.

TABLE 15

| Blend | Amount of blend added to die | Pressure | Tablet thickness | Observations |
|---|---|---|---|---|
| DBDMH/5 wt % MPP-611 | 5.0 g | 5000 psi | 0.389 in. | Intact tablet, smooth shiny surfaces |
| DBDMH/5 wt % Micropro 400 | 5.0 g | 5000 psi | 0.374 in. | Intact tablet, not 100% mold release from top punch |
| DBDMH | 2.5 g | 5000 psi | — | compact shattered and laminated on removal from die |
| CTB product | 2.5 g | 5000 psi | 0.22 in. | Intact tablet |

EXAMPLE 23

The 1,3-dibromo-5,5-dimethylhydantoin/5 wt % MPP-611 tablets produced in Example 22 were placed in glass beakers of water. The tablet appeared to do nothing. Its physical integrity remained intact as it slowly dissolved over a period of several months. In order to prove that it was releasing dissolved halogen, the tablet was removed from the water, washed with deionized water and dried with a paper towel. A plastic wash bottle was then used to wash the tablet into a deionized water solution containing N,N-diethyl-phenylenediamine (DPD) powder. This solution immediately turned pink when the wash water was introduced, proving that soluble halogen was being washed from the tablet. In this connection, DPD is an indicator of high sensitivity used to detect the presence of soluble halogen at the parts per million level. In the presence of such quantities of dissolved halogen, the DPD turns pink.

EXAMPLE 24

1,3-Dibromo-5,5-dimethylhydantoin was blended with micronized polyethylene wax (MPP-611) such that the blend contained 3 wt % of the wax. A sample of the blend (5 g) was introduced to a die made from Hastelloy® C alloy, and compacted to a pressure of 5000 psi. Three more samples (5 g each) were compacted in the same manner, and each time a single tablet was extracted from the die after the pressure had been released. In each case, before filling the die, its interior surfaces were lightly dusted with micronized polypropylene wax to serve as a lubricant. The tablets were manually broken into two equally-sized pieces. One half of each tablet was crushed into a powder with a mortar and pestle, and the powder was titrated to determine its wt % of active bromine. The other half of each tablet was placed in a sealed glass vial and placed in an oven at 50° C. After 30 days, the samples were removed from the oven, ground up, and titrated to determine its wt % of active bromine. For comparative purposes, a control sample of commercially produced 1,3-dibromo-5,5-dimethylhydantoin having an average particle size of about 64.5μ (containing no micronized polyethylene wax) was subjected to the same operations. In the case of this control sample, it was not possible to extract a single tablet from the die, and thus only shattered laminates could be tested.

Table 16 lists the results obtained for four samples of 1,3-dibromo-5,5-dimethylhydantoin/3 wt % micronized polyethylene wax blends, along with the control sample containing no additive.

TABLE 16

| | Wt % Active Bromine | |
|---|---|---|
| | Initial | After 30 days |
| Sample 1 | 53.4 | 53.3 |
| Sample 2 | 53.3 | 53.6 |

TABLE 16-continued

| | Wt % Active Bromine | |
|---|---|---|
| | Initial | After 30 days |
| Sample 3 | 54.2 | 53.3 |
| Sample 4 | 53.3 | 53.7 |
| Control | 55.3 | 55.2 |

The data in Table 16 indicate that, within the reproducibility of the analytical technique used, the presence of 3 wt % of micronized polyethylene wax in a 1,3-dibromo-5,5-dimethylhydantoin tablet does not induce a loss of active bromine after storage at 50° C. for 30 days. This absence of active bromine loss demonstrates the chemical compatibility of 1,3-dibromo-5,5-dimethylhydantoin and micronized polyethylene wax.

EXAMPLE 25

The strength of 1,3-dibromo-5,5-dimethylhydantoin tableted with different amounts of micronized polyethylene wax, as described in Example 22, was measured in a series of crush strength tests. In each test, 5 g of blended material was added to a die made from Hastelloy® C alloy and compressed with a screw-driven punch, also made from Hastelloy C alloy, to a pressure of 5000 psi. In each case, before filling the die, the interior surfaces of the die were lightly dusted with micronized polypropylene wax to serve as a lubricant. After extraction of the tablet from the die, a visual observation of the tablet was made. A Sintech® 1/S compression apparatus equipped with Testworks software was used to determine the crush strength of the tablets. This uses a screw-driven piston to exert pressure on the tablet until it breaks. The pressure required to reach the breaking point is recorded and reported as the crush strength.

The crush strength of the tablets was compared to a commercial toilet bowl product (abbreviated as CTB product in Table 17). This was purchased from a supermarket, ground to a powder and re-compacted under the conditions described above.

Table 17 summarizes the observations and results. The crush strength data represent an average of 3 separate measurements.

TABLE 17

| Blend | Average thickness | Average crush strength | Observations |
|---|---|---|---|
| DBDMH/5 wt % MPP-611 | 0.38 in. | 93.7 lb./in.* | Single tablets, shiny surfaces, low dust |
| DBDMH/3 wt % MPP-611 | 0.38 in. | 57.9 lb./in. | Single tablets, shiny surfaces, low dust |
| DBDMH/2 wt % MPP-611 | 0.37 in. | 37.0 lb./in. | Single tablets, shiny surface, low dust |
| CTB product | 0.44 in. | 55.2 lb./in. | Single tablets, dull surfaces, dusty |

*An estimate because 2 of the 3 tablets did not break before the limit of the load cell was exceeded.

The data in Table 17 clearly demonstrate that the crush strength of the tablets is a function of the micronized polyethylene wax loading, and that when using micronized polyethylene wax with 1,3-dibromo-5,5-dimethylhydantoin, it is possible to obtain a stronger product than a commercial toilet bowl product.

EXAMPLE 26

A series of different blends was prepared using a variety of micronized waxes (purchased from Micro Powders Incorporated, Tarrytown, N.Y.). Each blend was prepared in the fashion described in Example 20, such that the blend contained 3 wt % wax. The source of the DBDMH used in forming these blends was commercially produced 1,3-dibromo-5,5-dimethylhydantoin having an average particle size of about 64.5μ. Tableting and crush strength testing were performed as described in Examples 22 and 25.

The crush strength of the tablets was compared to a commercial toilet bowl product (abbreviated as CTB product in Table 18). This commercial toilet bowl product was purchased from a supermarket, ground to a powder, and re-tableted under the conditions described in Example 22.

Table 18 summarizes the observations and results. The crush strength data represent an average of 3 separate measurements.

TABLE 18

| DBDMH blend | Average thickness | Average crush strength | Observations |
|---|---|---|---|
| Polyfluo 200 wax | 0.38 in. | 30.2 lb/in. | Single tablets, tend to end-cap on breaking |
| Polyfluo 400 wax | 0.37 in. | 22.2 lb/in. | Single tablets, tend to end-cap on breaking |
| Micropro 400 wax | 0.36 in. | 11.8 lb/in. | Single tablets, tend to end-cap on breaking |
| Synfluo 180 VF | 0.38 in. | 37.8 lb/in. | Single tablets, tend to end-cap on breaking |
| Polysilk 600 | — | — | Powder is discolored, chemical incompatibility; no tablets were made |
| Handy Tack 140 resin | 0.39 in. | 27.5 lb/in. | Tablets are discolored, chemical incompatibility |
| CTB product | 0.44 in. | 102.3 lb/in. | Single tablets |

Although in the tests summarized in Table 18 the 1,3-dibromo-5,5-dimethylhydantoin tablets were not as strong as the prepared sample of CTB product, nevertheless all of the micronized waxes served as effective binders for 1,3-dibromo-5,5-dimethylhydantoin in that they produced whole tablets that remained intact when extracted from a die, and that exhibited adequate crush strength. However, a micronized modified petroleum resin (Handy Tack 140, Micro Powders Inc., Tarrytown, N.Y.) and a fluorinated hydrocarbon mixture (Polysilk 600, Micro Powders Inc., Tarrytown, N.Y.) both displayed signs of chemical incompatibility with 1,3-dibromo-5,5-dimethylhydantoin.

EXAMPLE 27

Blending and tableting studies were scaled up. A ribbon blender with a volume of two cubic feet was used to mix 25 kg of commercially produced 1,3-dibromo-5,5-dimethylhydantoin, having an average particle size of about 64.5μ, with micronized polyethylene wax (MPP-611) to achieve loadings of 2.0 wt % and 2.5 wt % of wax. The mixing time was 60 minutes in each case. A double-cone, tumble blender with a volume of 5 cubic feet was used to tumble mix 25 kg of 1,3-dibromo-5,5-dimethylhydantoin with micronized polyethylene wax to achieve a loading of 3 wt % of wax. The mixing time was 240 minutes.

Each blend was passed through a Chilsonator® breaker (The Fitzpatrick Company, Elmhurst, Ill.) and a set of screens to produce compacted granules of U.S. mesh size 12 to 18. Virgin, commercially-produced 1,3-dibromo-5,5-dimethylhydantoin having an average particle size of about 64.5μ, without micronized polyethylene wax, was also passed through the same equipment. This material did not compact and form granules. Instead, material exiting the Chilsonator® was mostly loose powder.

The granules of each 1,3-dibromo-5,5-dimethylhydantoin/micronized polyethylene wax blend were introduced to the feed hopper of a rotary tablet press. The turret contained 18 die cavities, each of which is 0.75 inches in diameter, which was automatically filled with granules and compressed between two punches made of Hastelloy® C alloy. The tablets ejected from the tablet press were collected, and 7 days later were subject to crush strength testing. The results given in Table 19 are an average of at least 3 tests.

TABLE 19

| DBDMH Blend | Tablet Thickness | Crush strength |
| --- | --- | --- |
| 2 wt % MPP-611, tumble blender | 0.49 in. | 16.6 lb/in |
| 2.5 wt % MPP-611, Ribbon blender | 0.49 in. | 19.3 lb/in |
| 3 wt % MPP-611, Ribbon blender | 0.72 in. | 24.1 lb/in |

The main findings from the runs of Example 27 were that the commercially produced 1,3-dibromo-5,5-dimethylhydantoin with an average particle size of about 64.5$\mu$ alone cannot be compacted into granules suitable for making tablets, and that the presence of micronized polyethylene wax (MPP-611) with such finely-divided 1,3-dibromo-5,5-dimethylhydantoin promotes the process of compaction into granules. These granules can be fed to a tableting machine and compacted into tablets. The strength of the tablets is governed by the amount of micronized polyethylene wax present. The higher the level of micronized polyethylene wax, the stronger the tablet.

EXAMPLE 28

The crush strength of tablets formed from a large average particle sized 1,3-dibromo-5,5-dimethylhydantoin formulated with a binder was measured. This 1,3-dibromo-5,5-dimethylhydantoin had an average particle size of about 189 microns, and the binder was a micronized polyethylene wax (MPP-611), and the binder was 3 wt % of the blend. The measurements were made utilizing a Sintech 1/S compression apparatus equipped with Testworks software. In these tests the tablets were subjected to increasing force applied along the longitudinal axis of the tablet until breakage occurred. The procedure for producing the tablets was as described in Example 22. The results of the crush strength tests are summarized in Table 20.

TABLE 20

| Tablet Thickness | Crush Strength | Crush Strength |
| --- | --- | --- |
| 0.372 in. | 39.8 lb. | 107.2 lb./in. |
| 0.375 in. | 44.9 lb. | 119.9 lb./in. |
| 0.375 in. | 37.5 lb. | 100.0 lb./in. |
| 0.375 in. | 36.1 lb. | 96.5 lb./in. |
| 0.377 in. | 37.6 lb. | 99.7 lb./in. |
| Averaged Results | 39.2 lb. | 104.6 lb./in. |

As can be seen from the foregoing description, there are a great number of important ways of carrying out or implementing this invention. In brief summary, some of these embodiments are as follows:

A) A method of effecting microbiocidal activity in a body of water, which method comprises providing in such body of water using a 1,3-dibromo-5,5-dialkylhydantoin microbiocidal agent described herein (DBDAH), most preferably 1,3-dibromo-5,5-dimethylhydantoin (DBDMH), a concentration of "free chlorine" that is greater than could be predicted from the concentration of "free chlorine" provided by an equimolar amount of N,N'-bromochloro-5,5-dimethylhydantoin (BCDMH), as determinable by comparative testing for "free chlorine" using Hach Method 8021 (copyright 1997, by Hach Company) and for "total chlorine" using Hach Method 8167 (copyright 1997, by Hach Company), and converting the mg/L $Cl_2$ "free chlorine" values from the tests to percentages of the mg/L $Cl_2$ "total chlorine" values from the tests, the four water samples used in said tests each having the same pH as said body of water and containing an equimolar quantity of BCDMH or DBDAH.

B) A method of A) above wherein the molar amount of the 1,3-dibromo-5,5-dialkyl-hydantoin microbiocidal agent (DBDAH), most preferably 1,3-dibromo-5,5-dimethylhydantoin, provided in said body of water is less than the molar amount of N,N'-bromochloro-5,5-dimethylhydantoin required to achieve the same degree of microbiological control.

C) Individual methods of A) or B) above wherein the 1,3-dibromo-5,5-dialkylhydantoin microbiocidal agent (DBDAH) used is 1,3-dibromo-5,5-dimethylhydantoin having (a) an average particle size in the range of about 20 to about 600 microns, (b) an average particle size of at least about 175 microns, (c) an average particle size of at least about 200 microns, (d) an average particle size of at least about 300 microns, or (e) an average particle size of at least about 400 microns.

D) Individual methods of A) or B) above wherein the 1,3-dibromo-5,5-dialkylhydantoin microbiocidal agent (DBDAH) used is (i) 1,3-dibromo-5,5-dimethylhydantoin in the form of a compacted product produced without a binder, or (ii) at least one 1,3-dibromo-5,5-dialkylhydantoin microbiocidal agent described herein (DBDAH), most preferably 1,3-dibromo-5,5-dimethylhydantoin, in the form of a compacted product produced using as a binder an amount of a micronized synthetic polyolefin-based hydrocarbon wax and/or a micronized synthetic polyfluorocarbon wax effective to form the compacted product, the wax being compatible with the 1,3-dibromo-5,5-dialkylhydantoin, or (iii) is in the form of a compacted product formed from at least one 1,3-dibromo-5,5-dialkylhydantoin microbiocidal agent described herein (DBDAH), most preferably 1,3-dibromo-5,5-dimethylhydantoin, wherein the compacted product was produced using as a binder an amount of a saturated, normally solid, fatty amide effective to form the compacted product.

E) Individual methods of (i) of D) above wherein the 1,3-dibromo-5,5-dimethylhydantoin being used has an average particle size of at least about 175, at least about 200, at least about 300, or at least about 400, microns.

F) Individual methods of (ii) of D) above wherein the wax is micronized polyethylene wax having, prior to compaction, an average particle size of no greater than about 15 microns, a maximum particle size of no greater than about 40 microns, and a density in the range of about 0.9 to about 1.4 grams per cc at 25° C.; or a micronized polyethylene wax that, prior to compaction, melts at a temperature in the range of about 109° C. to about 111° C.; or a micronized polypropylene wax having, prior to compaction, an average particle size in the range of about 5.0 to about 7.0 microns, a maximum particle size of about 22 microns, and a density in the range of about 0.9 to about 1.4 grams per cc at 25° C.; a micronized polypropylene wax that melts at a temperature in the range of about 140° C. to about 143° C., that has an average particle size in the range of about 5.0 to about 7.0 microns, and that has a maximum particle size of about 22 microns.

G) Individual methods of (iii) of D) above wherein the 1,3-dibromo-5,5-dialkylhydantoin being used is 1,3-dibromo-5,5-dimethylhydantoin having an average particle size of at least about 200, at least about 300, at least about 400, or at least about 500, microns.

H) Individual methods of A) or B) above wherein the microbiocidal activity in said body of water comprises combating *Escherichia coil* and/or *Enterococcus faecium* in said body of water.

I) A method of purveying a microbiological control agent for use in water in accordance with U.S. Environmental Protection Agency regulations, which method comprises purveying a container of a water control agent comprising at least one 1,3-dibromo-5,5-dialkylhydantoin microbiocidal agent described herein (DBDAH), most preferably 1,3-dibromo-5,5-dimethylhydantoin, the container bearing a label having thereon dosage levels pursuant to requirements promulgated by the U.S. Environmental Protection Agency, and specifying either on said label, or on or in packaging for said container, to the effect that the contents are recommended for use, or are for use, in water treatment, or to the effect that the contents are recommended for use, or are for use, in water having a pH of at least about 8.0.

J) Individual methods of H) or I) above wherein the 1,3-dibromo-5,5-dialkylhydantoin being used in H) or the control agent being used in I) is (i) 1,3-dibromo-5,5-dimethylhydantoin in the form of a compacted product produced without a binder, (ii) at least one 1,3-dibromo-5,5-dialkylhydantoin microbiocidal agent described herein (DBDAH), most preferably 1,3-dibromo-5,5-dimethylhydantoin, in the form of a compacted product produced using as a binder an amount of a micronized synthetic polyolefin-based hydrocarbon wax and/or a micronized synthetic polyfluorocarbon wax effective to form the compacted product, the wax being compatible with the 1,3-dibromo-5,5-dialkylhydantoin, or (iii) at least one 1,3-dibromo-5,5-dialkylhydantoin microbiocidal agent described herein (DBDAH), most preferably 1,3-dibromo-5,5-dimethylhydantoin, in the form of a compacted product formed from the 1,3-dibromo-5,5-dialkylhydantoin wherein the compacted product was produced using as a binder an amount of a saturated, normally solid, fatty amide effective to form the compacted product.

K) Individual methods of (i) of J) above wherein the 1,3-dibromo-5,5-dimethylhydantoin being used has an average particle size of at least about 175, at least about 200, at least about 300, or at least about 400, microns.

L) Individual methods of (ii) of J) above wherein the wax is polyethylene wax having, prior to compaction, an average particle size of no greater than about 15 microns, a maximum particle size of no greater than about 40 microns, and a density in the range of about 0.9 to about 1.4 grams per cc at 25° C.; or wherein the wax is a polyethylene wax that, prior to compaction, melts at a temperature in the range of about 109° C. to about 111° C.; or wherein the wax is polypropylene wax having, prior to compaction, an average particle size in the range of about 5.0 to about 7.0 microns, a maximum particle size of about 22 microns, and a density in the range of about 0.9 to about 1.4 grams per cc at 25° C.; or wherein the wax, prior to compaction, is a polypropylene wax that melts at a temperature in the range of about 140° C. to about 143° C., that has an average particle size in the range of about 5.0 to about 7.0 microns, and that has a maximum particle size of about 22 microns.

M) Individual methods of (iii) of J) above wherein the 1,3-dibromo-5,5-dialkylhydantoin used in forming the compacted product is 1,3-dibromo-5,5-dimethylhydantoin having an average particle size of at least about 200, at least about 300, or at least about 400, microns.

N) Individual methods of any of A)-M) above wherein the body of water being treated is industrial cooling water, wastewater, or process water.

O) A method of N) above wherein the treatment of the water comprises passing a sidestream of the water through a bed of the 1,3-dibromo-5,5-dialkylhydantoin such that a biocidally effective amount of the 1,3-dibromo-5,5-dialkylhydantoin is delivered to the water.

P) Individual methods of I) above wherein the microbiological control agent is purveyed for use in at least cooling water, wastewater, or process water.

Q) Individual methods of A) or B) above wherein the microbiocidal activity in said body of water comprises eradicating, substantially eradicating, or reducing biofilm on a surface in contact with said body of water.

R) Individual methods of Q) above wherein the 1,3-dibromo-5,5-dialkylhydantoin being used is 1,3-dibromo-5,5-dimethylhydantoin having (a) an average particle size in the range of about 20 to about 600 microns, (b) an average particle size of at least about 175 microns, (c) an average particle size of at least about 200 microns, (d) an average particle size of at least about 300 microns, or (e) an average particle size of at least about 400 microns.

S) Individual methods of Q) above wherein the 1,3-dibromo-5,5-dialkylhydantoin being used is (i) 1,3-dibromo-5,5-dimethylhydantoin in the form of a compacted product produced without a binder, or (ii) at least one 1,3-dibromo-5,5-dialkylhydantoin described herein (DBDAH), most preferably 1,3-dibromo-5,5-dimethylhydantoin, in the form of a compacted product produced using as a binder an amount of a micronized synthetic polyolefin-based hydrocarbon wax and/or a micronized synthetic polyfluorocarbon wax effective to form the compacted product, the wax being compatible with the 1,3-dibromo-5,5-dialkylhydantoin, or (iii) at least one 1,3-dibromo-5,5-dialkylhydantoin described herein (DBDAH), most preferably 1,3-dibromo-5,5-dimethylhydantoin, in the form of a compacted product formed from the 1,3-dibromo-5,5-dialkylhydantoin wherein the compacted product was produced using as a binder an amount of a saturated, normally solid, fatty amide effective to form the compacted product.

T) Individual methods of (i) of S) above wherein the 1,3-dibromo-5,5-dimethylhydantoin being used has an average particle size of at least about 175, at least about 200, at least about 300, or at least about 400, microns.

U) Individual methods of (ii) of S) above wherein the wax is micronized polyethylene wax having, prior to compaction, an average particle size of no greater than about 15 microns, a maximum particle size of no greater than about 40 microns, and a density in the range of about 0.9 to about 1.4 grams per cc at 25° C.; or a micronized polyethylene wax that, prior to compaction, melts at a temperature in the range of about 109° C. to about 111° C.; or a micronized polypropylene wax having, prior to compaction, an average particle size in the range of about 5.0 to about 7.0 microns, a maximum particle size of about 22 microns, and a density in the range of about 0.9 to about 1.4 grams per cc at 25° C.; a micronized polypropylene wax that melts at a temperature in the range of about 140° C. to about 143° C., that has an average particle size in the range of about 5.0 to about 7.0 microns, and that has a maximum particle size of about 22 microns.

V) Individual methods of (iii) of S) above wherein the 1,3-dibromo-5,5-dialkylhydantoin being used is 1,3-dibromo-5,5-dimethylhydantoin having an average particle size of at least about 200, at least about 300, at least about 400, or at least about 500, microns.

W) Individual methods of A) or B) above wherein the microbiocidal activity in said body of water comprises eradicating, substantially eradicating, or at least reducing *Pseudomonas aeruginosa* biofilm on a surface in contact with said body of water.

X) A method of purveying a biofilm control agent for use in water in accordance with U.S. Environmental Protection Agency regulations, which method comprises purveying a container of a biofilm control agent for use in aqueous media, such agent comprising at least one 1,3-dibromo-5,5-dialkylhydantoin described herein (DBDAH), most preferably 1,3-dibromo-5,5-dimethylhydantoin, the container bearing a label having thereon dosage levels pursuant to requirements promulgated by the U.S. Environmental Protection Agency, and specifying either on said label, or on or in packaging for said container, to the effect that the contents are recommended for use, or are for use, with water having a pH of at least about 8.0.

Still other embodiments of this invention include the following:

A1) A method of sanitizing a body of water which comprises dispensing into the water, from a dispenser apparatus that automatically dispenses into the water at a controlled rate biocidal species from a charge of biocidal agent contained therein, biocidal species formed by interaction between water and at least one 1,3-dibromo-5,5-dialkylhydantoin in which one of the alkyl groups in the 5-position is a methyl group and the other alkyl group in the 5-position has in the range of 1 to 4 carbon atoms, wherein said at least one 1,3-dibromo-5,5-dialkylhydantoin as charged into said dispenser apparatus is in the form of granules that are able to be dissolved in quiescent water that is at a temperature of 25° C. at a rate such that 60 minutes after initial contact, the water contains in the range of about 75 to about 430 mg/L of "free chlorine" per gram of granules.

A2) A method of sanitizing a body of water which comprises dispensing into the water, from a dispenser apparatus that automatically dispenses into the water at a controlled rate biocidal species from a charge of biocidal agent contained therein, biocidal species formed by interaction between water and at least one 1,3-dibromo-5,5-dialkylhydantoin in which one of the alkyl groups in the 5-position is a methyl group and the other alkyl group in the 5-position has in the range of 1 to 4 carbon atoms, wherein said at least one 1,3-dibromo-5,5-dialkylhydantoin as charged into said dispenser apparatus is in the form of granules that have an average crush strength of at least about 15 pounds per inch of thickness and an average size in the range of about 40 U.S. standard mesh size to about ⅜-inch.

A3) A method of sanitizing a body of water which comprises dispensing into the water, from a dispenser apparatus that automatically dispenses into the water at a controlled rate biocidal species from a charge of biocidal agent contained therein, biocidal species formed by interaction between water and at least one 1,3-dibromo-5,5-dialkylhydantoin in which one of the alkyl groups in the 5-position is a methyl group and the other alkyl group in the 5-position has in the range of 1 to 4 carbon atoms, wherein said at least one 1,3-dibromo-5,5-dialkylhydantoin as charged into said dispenser apparatus is in the form of granules that (i) have an average crush strength of at least about 15 pounds per inch of thickness and (ii) have an average size in the range of about 40 U.S. standard mesh size to about ⅜-inch; and (iii) that are able to be dissolved in quiescent water that is at a temperature of 25° C. at a rate such that 60 minutes after initial contact, the water contains in the range of about 75 to about 430 mg/L of "free chlorine" per gram of granules.

A4) A method according to any of A1), A2), or A3) wherein said at least one 1,3-dibromo-5,5-dialkylhydantoin is 1,3-dibromo-5,5-dimethylhydantoin.

A5) A method according to any of A1), A2), or A3) wherein said at least one 1,3-dibromo-5,5-dialkylhydantoin comprises 1,3-dibromo-5-isobutyl-5-methylhydantoin, 1,3-dibromo-5-n-propyl-5-methylhydantoin, or 1,3-dibromo-5-ethyl-5-methylhydantoin, or at least any two thereof.

A6) A method according to any of A1), A2), or A3) wherein said at least one 1,3-dibromo-5,5-dialkylhydantoin is 1,3-dibromo-5,5-dimethylhydantoin and 1,3-dibromo-5-ethyl-5-methylhydantoin.

A7) A method according to any of A1), A2), or A3) wherein said dispenser apparatus is a floater-type dispenser as described and claimed in each of the respective claims of U.S. Pat. No. 5,476,116.

A8) A method according to any of A1), A2), or A3) wherein said dispenser apparatus is a dispenser as described and claimed in each of the respective claims of U.S. Pat. No. 4,617,117.

A9) A method according to any of A1), A2), or A3) wherein said dispenser apparatus is a dispenser as described and claimed in each of the respective claims of U.S. Pat. No. 5,089,127.

A10) A method according to any of A7), A8), or A9) wherein said at least one 1,3-dibromo-5,5-dialkylhydantoin is 1,3-dibromo-5,5-dimethylhydantoin.

A11) A method according to any of A7), A8), or A9) wherein said at least one 1,3-dibromo-5,5-dialkylhydantoin comprises 1,3-dibromo-5-isobutyl-5-methylhydantoin, 1,3-dibromo-5-n-propyl-5-methylhydantoin, or 1,3-dibromo-5-ethyl-5-methylhydantoin, or at least any two thereof.

A12) A method according to any of A7), A8), or A9) wherein said at least one 1,3-dibromo-5,5-dialkylhydantoin is 1,3-dibromo-5,5-dimethylhydantoin and 1,3-dibromo-5-ethyl-5-methylhydantoin.

A13) Apparatus for sanitizing a body of water which comprises a dispenser apparatus that automatically dispenses into the water at a controlled rate biocidal species from a charge of biocidal agent contained therein, and a charge therein of at least one 1,3-dibromo-5,5-dialkylhydantoin in which one of the alkyl groups in the 5-position is a methyl group and the other alkyl group in the 5-position has in the range of 1 to 4 carbon atoms, wherein said at least one 1,3-dibromo-5,5-dialkylhydantoin as charged into said dispenser apparatus is in the form of granules that are able to be dissolved in quiescent water that is at a temperature of 25° C. at a rate such that 60 minutes after initial contact, the water contains in the range of about 75 to about 430 mg/L of "free chlorine" per gram of granules.

A14) Apparatus for sanitizing a body of water which comprises a dispenser apparatus that automatically dispenses into the water at a controlled rate biocidal species from a charge of biocidal agent contained therein, and a charge therein of at least one 1,3-dibromo-5,5-dialkylhydantoin in which one of the alkyl groups in the 5-position is a methyl group and the other alkyl group in the 5-position has in the range of 1 to 4 carbon atoms, wherein said at least one 1,3-bromo-5,5-dialkylhydantoin as charged into said dispenser apparatus is in the form of granules that have an average crush strength of at least about 15 pounds per inch of thickness and an average size in the range of about 40 U.S. standard mesh size to about ⅜-inch.

A15) Apparatus for sanitizing a body of water which comprises a dispenser apparatus that automatically dispenses into the water at a controlled rate biocidal species from a charge of biocidal agent contained therein, and a charge therein of at least one 1,3-dibromo-5,5-dialkylhydantoin in which one of the alkyl groups in the 5-position is a methyl group and the other alkyl group in the 5-position has in the range of 1 to 4 carbon atoms, wherein said at least one 1,3-dibromo-5,5-dialkylhydantoin as charged into said dispenser apparatus is in the form of granules that (i) have an average crush strength of at least about 15 pounds per inch of thickness and (ii) have an average size in the range of about 40 U.S. standard mesh size to about ⅜-inch and (iii) that are able to be dissolved in quiescent water that is at a temperature of 25° C. at a rate such that 60 minutes after initial contact, the water contains in the range of about 75 to about 430 mg/L of "free chlorine" per gram of granules.

A16) Apparatus according to any of A13), A14), or A15) wherein said at least one 1,3-dibromo-5,5-dialkylhydantoin is 1,3-dibromo-5,5-dimethylhydantoin.

A17) Apparatus according to any of A13), A14), or A15) wherein said at least one 1,3-dibromo-5,5-dialkylhydantoin comprises 1,3-dibromo-5-isobutyl-5-methylhydantoin, 1,3-dibromo-5-n-propyl-5-methylhydantoin, or 1,3-dibromo-5-ethyl-5-methylhydantoin, or at least any two thereof.

A18) Apparatus according to any of A13), A14), or A15) wherein said at least one 1,3-dibromo-5,5-dialkylhydantoin is 1,3-dibromo-5,5-dimethylhydantoin and 1,3-dibromo-5-ethyl-5-methylhydantoin.

A19) Apparatus according to any of A13), A14), or A15) wherein said dispenser apparatus is a floater-type dispenser capable of dispensing in the range of about 0.5 to about 2 pounds per week of said 1,3-dibromo-5,5-dialkylhydantoin.

A20) Apparatus according to any of A13), A14), or A15) wherein said dispenser apparatus is a dispenser as described and claimed in each of the respective claims of U.S. Pat. No. 4,617,117.

A21) A method according to any of A13), A14), or A15) wherein said dispenser apparatus is a dispenser as described and claimed in each of the respective claims of U.S. Pat. No. 5,089,127.

A22) A method according to any of A19), A20), or A21) wherein said at least one 1,3-dibromo-5,5-dialkylhydantoin is 1,3-dibromo-5,5-dimethylhydantoin.

A23) A method according to any of A19), A20), or A21) wherein said at least one 1,3-dibromo-5,5-dialkylhydantoin comprises 1,3-dibromo-5-isobutyl-5-methylhydantoin, 1,3-dibromo-5-n-propyl-5-methylhydantoin, or 1,3-dibromo-5-ethyl-5-methylhydantoin, or at least any two thereof.

A24) A method according to any of A19), A20), or A21) wherein said at least one 1,3-dibromo-5,5-dialkylhydantoin is 1,3-dibromo-5,5-dimethylhydantoin and 1,3-dibromo-5-ethyl-5-methylhydantoin.

References herein to biofilm on a surface in contact with an aqueous medium or water, are not to be construed as requiring the aqueous medium or water to be in constant contact with such surface. As long as the aqueous medium or water comes into contact with a surface often enough to result in the formation of biofilm on such surface, it is within the scope of this invention to treat such aqueous medium or water pursuant to this invention so as to combat such biofilm. For example, this invention includes treatment of aqueous media or water that is splashed, sprayed, or dripped on or against a surface with sufficient frequency for biofilm to develop on such surface. It is also to be understood that the aqueous medium or the water can contain any of a variety of contaminants and/or impurities. The only requirements are that such aqueous medium or water periodically or constantly contacts a surface such that the formation of biofilm occurs on the surface, and that the contaminants and/or impurities in the aqueous medium or water do not prevent the 1,3-dibromo-5,5-dialkylhydantoin(s) such as 1,3-dibromo-5,5-dimethylhydantoin, from eradicating, or at least reducing the amount of, the biofilm on such surface.

As used herein, including the claims, the term "purveying" means carrying out or causing to be carried out one or more of the following activities: advertising, marketing, promoting for sale, offering for sale, selling, bartering, trading, leasing, merchandising, importing, exporting, dealing in commerce with, supplying, distributing, delivering, and any and all other activities of similar import.

As used herein, including the claims, the terms "aqueous medium" and "water" refer to and include any liquid in which the predominate liquid component is water. Such aqueous medium or water may contain various other materials, whether organic or inorganic, or both, and is exemplified by recreational water, industrial cooling water, process water and wastewater. As is well known in the art, if the water has a pH of at least about 8, it is not included in the category of recreational water, at least at the present time in the United States.

The term "biocidally effective amount" or terms of similar meaning used herein refer to amounts that are sufficient to kill at least a significant portion of microbiological species such as planktonic bacteria, biofilm bacteria, algea, or the like. It does not denote that the substance used in should kill other types of life such as animals, birds or the like.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

It will also be understood that the terms "substantial" and "substantially" denote that chemical operations or treatments ordinarily do not involve absolutes. Thus instead of describing a variable or a result as an absolute, it is far more realistic to describe the variable or result as being in the substantial vicinity of the expressed variable or result. For example when describing eradication of an organism, it can be more realistic to refer to the substantial eradication of the organism rather than to imply that absolute total eradication occurs, since one skilled in the art fully realizes that a substantial kill is a very desirable result, and the possibility always exists that even if a small portion of the organism survives the treatment, the overall result is nevertheless highly beneficial in most cases. Likewise the terms "substantially continuous" and "substantially continuously" are realistic expressions since interruptions in delivering microbiocide to the water is entirely acceptable provided of course that the interruption is not of such duration as would completely negate effective microbiocidal activity when relying upon substantially continuous delivery of the biocide to the water to provide such activity. Thus this document should be read with the application of common sense.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method of achieving an effective "free chlorine" level in treating with a biocide water that is in contact with, or that comes into contact with, at least one iron or copper surface, which method comprises introducing into said water a biocidally effective amount of at least one biocide consisting essentially of 1,3-dibromo-5,5-dialkylhydantoin wherein said amount (i) provides in the water a biocidally effective "free chlorine" level that is within 90% of the "total chlorine" level in the water thereby enabling the rate of said 1,3-dibromo-5,5-dialkylhydantoin biocide consumption to be reduced as compared to N,N'-bromochloro-5,5-dimethylhydantoin, and (ii) reduces the rate of corrosion of said iron or copper with which the water is or comes into contact as compared to N,N'-bromochloro-5,5-dimethylhydantoin, said at least one 1,3-dibromo-5,5-dialkylhydantoin that is introduced into said water being characterized in that one of the alkyl groups in the 5-position is a methyl group and the other alkyl group in the 5-position has in the range of 1 to 4 carbon atoms.

2. A method according to claim 1 wherein said at least one 1,3-dibromo-5,5-dialkylhydantoin that is introduced into said water is 1,3-dibromo-5,5-dimethylhydantoin.

3. A method according to claim 1 wherein said at least one 1,3-dibromo-5,5-dialkylhydantoin is introduced continuously or substantially continuously into said water from a dispenser containing and dispensing said at least one 1,3-dibromo-5,5-dialkylhydantoin at a rate that maintains in the water said biocidally effective amount.

4. A method according to claim 3 further comprising periodically charging said dispenser with granules of said at least one 1,3-dibromo-5,5-dialkylhydantoin that are able to be dissolved and dispensed from said dispenser at a rate that maintains in the water said biocidally effective amount.

5. A method according to claim 4 wherein said dispenser is a floater-type dispenser.

6. A method according to any of claim 4 or 5 wherein said at least one 1,3-dibromo-5,5-dialkylhydantoin that is introduced into said water is 1,3-dibromo-5,5-dimethylhydantoin, and wherein said granules of 1,3-dibromo-5,5-dialkylhydantoin are able to be dissolved in quiescent water that is at a temperature of 25° C. at a rate such that 60 minutes after initial contact, the water contains in the range of about 75 to about 430 mg/L of "free chlorine" per gram of granules.

7. A method according to any of claim 4 or 5 wherein said at least one 1,3-dibromo-5,5-dialkylhydantoin that is introduced into said water is 1,3-dibromo-5,5-dimethylhydantoin, and wherein prior to introduction into said water said granules of 1,3-dibromo-5,5-dialkylhydantoin have an average crush strength of at least about 15 pounds per inch of thickness and an average size in the range of about 40 U.S. standard mesh size to about ⅜-inch.

8. A method of achieving an effective "free chlorine" level in treating with a biocide water that is or that comes into contact with at least one iron or copper surface, which method comprises treating said water with a biocide consisting essentially of at least one 1,3-dibromo-5,5-dialkyihydantoin at a rate that (i) provides in the water a biocidally effective "free chlorine" level, (ii) reduces the rate of corrosion of said iron or copper with which the water is or comes into contact as compared to N,N'-bromochloro-5,5-dimethylhydantoin, and (iii) provides in the water a "free chlorine" level that is within 90% of the "total chlorine" level in the water thereby enabling the rate of biocide consumption in treating said water to be reduced as compared to N,N'-bromochloro-5,5-dimethylhydantoin, said at least one 1,3-dibromo-5,5-dialkylhydantoin that is introduced into said water being characterized in that one of the alkyl groups in the 5-position is a methyl group and the other alkyl group in the 5-position has in the range of 1 to 4 carbon atoms.

9. A method according to claim 8 wherein said at least one 1,3-dibromo-5,5-dialkylhydantoin that is used to treat said water is 1,3-dibromo-5,5-dimethylhydantoin.

10. A method according to claim 8 wherein said at least one 1,3-dibromo-5,5-dialkylhydantoin is introduced continuously or substantially continuously into said water from a dispenser containing and dispensing said at least one 1,3-dibromo-5,5-dialkylhydantoin at a rate that maintains in the water said biocidally effective "free chlorine" level.

11. A method according to claim 10 further comprising periodically charging said dispenser with granules of said at least one 1,3-dibromo-5,5-dialkylhydantoin that are adapted to be dissolved and dispensed from said dispenser at a rate that maintains in the water said biocidally effective "free chlorine" level.

12. A method according to claim 11 wherein said dispenser is a floater-type dispenser.

13. A method according to claim 11 wherein said dispenser is an in-line or off-line type dispenser.

14. A method according to any of claim 11, 12, or 13 wherein said at least one 1,3-dibromo-5,5-dialkylhydantoin that is introduced into said water is 1,3-dibromo-5,5-dimethylhydantoin, and wherein said granules of 1,3-dibromo-5,5-dialkylhydantoin are able to be dissolved in quiescent water that is at a temperature of 25° C. at a rate such that 60 minutes after initial contact, the water contains in the range of about 75 to about 430 mg/L of "free chlorine" per gram of granules.

15. A method according to claim 8 wherein said at least one 1,3-dibromo-5,5-dialkylhydantoin that is introduced into said water comprises 1,3-dibromo-5-isobutyl-5-methylhydantoin, 1,3-dibromo-5-n-propyl-5-methylhydantoin, or 1,3-dibromo-5-ethyl-5-methylhydantoin, or at least any two thereof.

16. A method according to claim 8 wherein said at least one 1,3-dibromo-5,5-dialkylhydantoin that is introduced into said water is 1,3-dibromo-5,5-dimethylhydantoin and 1,3-dibromo-5-ethyl-5-methylhydantoin.

17. A method according to claim 9 wherein the water that is in contact with, or that comes into contact with, at least one iron or copper surface, also is in contact with biofilm, or comes into contact with biofilm, and wherein said effective biocidally active amount of 1,3-dibromo-5,5-dimethylhydantoin results in eradication or at least effective biocidal challenge of said biofilm to a greater extent than would be accomplished by an equimolar quantity of N,N'-bromochloro-5,5-dimethylhydantoin.

18. A method of effecting microbiocidal activity in a body of water that is in contact with, or that comes into contact with, at least one iron or copper surface, which method comprises providing in said body of water by use of a biocide consisting essentially of at least one 1,3-dibromo-5,5-dialkylbydantoin, a concentration of "free chlorine" that (A) is greater than could be predicted from the concentration of "free chlorine" provided by an equimolar amount of N,N'-bromochloro-5,5-dimethylhydantoin, and (B) results in less corrosion of said at least one iron or copper surface as compared to an equal concentration of free chlorine from N,N'-bromochloro-5,5-dimethylhydantoin, said at least one 1,3-dibromo-5,5-dialkylhydantoin that is used being characterized in that one of the alkyl groups in the 5-position is a methyl group and the other alkyl group in the 5-position has in the range of 1 to 4 carbon atoms.

19. A method according to claim 18 wherein said at least one 1,3-dibromo-5,5-dialkylhydantoin that is used is 1,3-dibromo-5,5-dimethylhydantoin.

20. A method according to claim 18 wherein said at least one 1,3-dibromo-5,5-dialkylhydantoin that is used enables the rate of biocide consumption in treating said water to be reduced as compared to N,N'-bromochloro-5,5-dimethylhydantoin.

21. A method according to claim 20 wherein said at least one 1,3-dibromo-5,5-dialkylhydantoin that is used is 1,3-dibromo-5,5-dimethylhydantoin.

22. A method according to claim 18 wherein prior to use said at least one 1,3-dibromo-5,5-dialkylhydantoin that is used is in the form of granules free of hydrophobic binder, which granules have an average crush strength of at least 15 pounds per inch of granule thickness, and an average size in the range of about 40 U.S. standard mesh size to about ⅜-inch.

23. A method according to claim 22 wherein said at least one 1,3-dibromo-5,5-dialkylhydantoin that is used in the form of granules is 1,3-dibromo-5,5-dimethylhydantoin.

24. A method according to any of claim 22 or 23 wherein prior to use said granules are devoid of any added component contributing crush strength or binding action to the granules, and wherein prior to use said granules have an average crush strength of at least 20 pounds per inch of granule thickness.

* * * * *